United States Patent
Anaclerio et al.

(10) Patent No.: US 6,872,730 B2
(45) Date of Patent: Mar. 29, 2005

(54) SUBSTITUTED BENZOFURANS AND BENZOTHIOPHENES, METHODS OF MAKING AND METHODS OF USE AS INTEGRIN ANTAGONISTS

(75) Inventors: Beth M. Anaclerio, New Castle, DE (US); Juan J. Marugan Sanchez, Downingtown, PA (US); Victor J. Marder, Los Angeles, CA (US); David C. U'Prichard, Philadelphia, PA (US); Bruce E. Tomczuk, Collegeville, PA (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 8 days.

(21) Appl. No.: 10/132,706

(22) Filed: Apr. 26, 2002

(65) Prior Publication Data

US 2003/0018064 A1 Jan. 23, 2003

Related U.S. Application Data

(60) Provisional application No. 60/324,516, filed on Sep. 26, 2001, and provisional application No. 60/286,532, filed on Apr. 27, 2001.

(51) Int. Cl.$^7$ .............. A61K 31/381; A61K 31/4375; A61K 31/5383; C07D 409/12; C07D 471/04
(52) U.S. Cl. .............. 514/300; 514/230.5; 514/337; 514/314; 514/443; 514/275; 514/259; 514/249; 514/243; 514/248; 514/367; 514/394; 514/303; 514/301; 544/105; 544/183; 544/236; 544/279; 544/331; 544/350; 546/122; 546/113; 546/114; 546/118; 546/174; 546/281.1; 548/159; 548/194; 548/305.1; 549/51; 549/57; 549/58
(58) Field of Search .................. 546/122, 281.1, 546/174, 113, 114, 118; 544/331, 183, 236, 279, 350, 105; 548/159, 194, 305.1; 549/51, 57, 58; 514/300, 337, 314, 443, 275, 259, 249, 248, 243, 367, 394, 303, 301, 230.5

(56) References Cited

U.S. PATENT DOCUMENTS

| | | | |
|---|---|---|---|
| 5,223,517 A | 6/1993 | Muller et al. | |
| 5,290,788 A | 3/1994 | Stevens et al. | |
| 5,741,796 A | 4/1998 | Hartman et al. | |
| 5,744,488 A | 4/1998 | Cross et al. | |
| 6,066,648 A | 5/2000 | Duggan et al. | |
| 6,184,238 B1 | 2/2001 | Takano et al. | |

FOREIGN PATENT DOCUMENTS

| | | |
|---|---|---|
| EP | 0 623 607 A1 | 11/1994 |
| WO | WO 97/06791 | 2/1997 |
| WO | WO 97/23451 | 7/1997 |
| WO | WO 97/36859 | 10/1997 |
| WO | WO 97/45137 | 12/1997 |
| WO | WO 98/00395 | 1/1998 |
| WO | WO 99/30713 | 6/1999 |
| WO | WO 00/02874 | 1/2000 |
| WO | WO 00/33838 | 6/2000 |
| WO | WO 00/38719 | 7/2000 |
| WO | WO 01/58893 A2 | 8/2001 |

OTHER PUBLICATIONS

Batt et al., J. Med. Chem. 2000, 43:41–58.*
Albelda, S.M. "Biology of Disease. Role of Integrins and Other Cell Adhesion Molecules in Tumor Progression and Metastasis," *Lab. Invest.* 68:4–17, The United States and Canadian Academy of Pathology, Inc. (1993).
Albelda, S.M., et al., "Integrin Distribution in Malignant Melanoma: Association of the $\beta_3$ Subunit with Tumor Progression," *Cancer Res.* 50:6757–6764, American Association for Cancer Research (1990).
Boudreau, N., and Rabinovitch M., "Developmentally Regulated Changes in Extracellular Matrix in Endothelial and Smooth Muscle Cells in the Ductus Arteriosus May be Related to Intimal Proliferation," *Lab. Invest.* 64:187–199, The United States and Canadian Academy of Pathology, Inc. (1991).
Brocke, S., et al., "Antibodies to CD44 and integrin $\alpha_4$, but not L–selectin, prevent central nervous system inflammation and experimental encephalomyelitis by blocking secondary leukocyte recruitment," *Proc. Natl. Acad. Sci. USA* 96:6896–6901, The National Academy of Sciences (1999).
Brooks, P.C., et al., "Integrin $\alpha_v\beta_3$ Antagonists Promote Tumor Regression by Inducing Apoptosis of Angiogenic Blood Vessels," *Cell* 79:1157–1164, Cell Press (1994).
Brooks, P.C., "Integrin $\alpha v\beta 3$: A Therapeutic Target," *DN&P* 10:456–461, Prous Science (1997).

(List continued on next page.)

*Primary Examiner*—Evelyn Mei Huang
(74) *Attorney, Agent, or Firm*—Woodcock Washburn LLP

(57) ABSTRACT

The present invention relates to novel substituted benzofurans and benzothiophenes compounds that are antagonists of alpha V ($\alpha v$) integrins, for example $\alpha_v\beta_3$ and $\alpha_v\beta_5$ integrins, their pharmaceutically acceptable salts, and pharmaceutical compositions thereof. The compounds may be used in the treatment of pathological conditions mediated by $\alpha_v\beta_3$ and $\alpha_v\beta_5$ integrins, including such conditions as tumor growth, metastasis, restenosis, osteoporosis, inflammation, macular degeneration, diabetic retinopathy, and rheumatoid arthritis. The compounds have the general formula I:

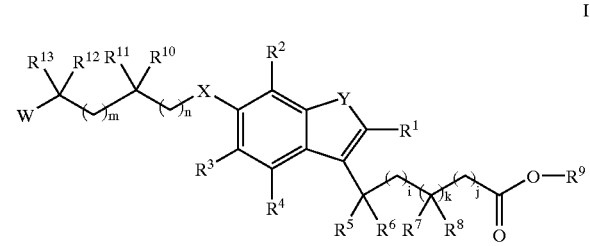

where $R^1, R^2, R^3, R^4, R^5, R^6, R^7, R^8, R^9, R^{10}, R^{11}, R^{12}, R^{13}, R^{14}$, m, n, i, j and k are defined herein.

20 Claims, No Drawings

OTHER PUBLICATIONS

Brooks, P.C., et al., "Antiintegrin αvβ3 blocks human breast cancer growth and angiogenesis in human skin," *J. Clin. Invest.* 96:1815–1822, The American Society for Clinical Investigation, Inc. (1995).

Brooks, P.C., et al., "Requirement of Vascular Integrin αvβ$_3$ for Angiogenesis," *Science* 265:569–571, American Association for the Advancement of Science (1994).

Brooks, P.C., "Cell Adhesion molecules in angiogenesis," *Cancer Met. Rev.* 15:187–194, Kluwer Academic Publishers (1996).

Chemical Abstracts English language summary of WO 98/00395 (Document AP1), CAPLUS Accession No. 1998:38464.

Cheresh, D.A., "Structure, function and biological properties of integrin of α$_v$β$_3$ on human melanoma cells," *Cancer Met. Rev.* 10:3–10, Kluwer Academic Publishers (1991).

Choi, E.T., et al., "Inhibition of neointimal hyperplasia by blocking α$_v$β$_3$ integrin with a small peptide antagonist GpenGRGDSPCA," *J. Vasc. Surg.* 19:125–134, Mosby-Year Book (1994).

Dennis, M.S., et al., "Binding Interactions of Kistrin With Platelet Glycoprotein IIb–IIIa: Analysis by Site–Directed Mutagenesis," *Proteins* 15:312–321, Wiley–Liss (1993).

Dialog File 351, Accession No. 14058279, Derwent WPI English language abstract for WO 01/58893 (Document AN2).

Enenstein, J., and Kramer, R.H., "Confocal Microscopic Analysis of Integrin Expression on the Microvasculature and its Sprouts in the Neonatal Foreskin," *J. Invest. Dermatol.* 103:381–386, The Society for Investigative Dermatology, Inc. (1994).

Fisher, J.E., et al., "Inhibition of Osteoclastic Bone Resorption In Vivo by Echistatin, an "Arginyl–Glycyl–Aspartyl" (RGD)–Containing Protein," *Endocrinology* 132:1411–1413, The Endocrine Society (1993).

Friedlander, M., et al., "Definition of Two Angiogenic Pathways by Distinct α$_v$Integrins," *Science* 270:1500–1502, American Association for the Advancement of Science (1995).

Gladson, C.L., "Expression of Integrin αvβ3 in Small Blood Vessels of Glioblastoma Tumors," *J. Neuropathol. Exp. Neurol.* 55:1143–1149, The American Association of Neuropathologists (1996).

Greene, T.W., and Wuts, P.G.M., "Special –NH Protective Groups. Protection for the Amino Group: Special –NH Protective Groups," in *Protective Groups in Organic Synthesis*, 2nd edition, John Wiley, and Sons, Inc. New York, pp. 267–287 and p. 331 (1991).

Greenspoon, N., et al., "Structural Analysis of Integrin Recognition and the Inhibition of Integrin–Mediated Cell Functions by Novel Nonpeptidic Surrogates of the Arg–Gly–Asp Sequence," *Biochemistry* 32:1001–1008, The American Chemical Society (1993).

Hardan, I., et al., "Inhibition of Metastatic Cell Colonization in Murine Lungs and Tumor–Induced Morbidity by Non–Peptidic Arg–Gly–Asp Mimetics," *Int. J. Cancer* 55:1023–1028, Wiley–Liss, Inc. (1993).

Hershkovits, R., et al., "Inhibition of CD4$^+$T lymphocyte binding to fibronectin and immune–cell accumulation in inflammatory sites by non–peptidic mimetics of Arg–Gly–Asp," *Clin. Exp. Immunol.* 95:270–276, Blackwell Scientific Publishers (1994).

Horton, M., "Current Status Review. Vitronectin receptor: tissue specific expression or adaption to culture?" *Int. J. Exp. Pathol.* 71:741–759, Blackwell Scientific Publications (1990).

Hynes, R.O., "Integrins: Versatility, Modulation, and Signaling in Cell Adhesion," *Cell* 69:11–25, Cell Press (1992).

Juliano, R., "Signal transduction by integrins and its role in the regulation of tumor growth," *Cancer Met. Rev.* 13:25–30, Kluwer Academic Publishers (1994).

Kaul, D.K., et al., "Monoclonal antibodies to αvβ3 (7E3 and LM609) inhibit sickle red blood cell–endothelium interactions induced by platelet–activating factor," *Blood* 95:368–374, The American Society of Hematology (Jan. 2000).

Ku, T.W., et al., "Direct Design of a Potent Non–Peptide Fibrinogen Receptor Antagonist Based on the Structure and Conformation of a Highly Constrained Cyclic RGD Peptide," *J. Amer. Chem. Soc.* 115:8861–8862, The American Chemical Society (1993).

Marquardt, D.W., "An Algorithm for Least–Squares Estimation of Nonlinear Parameters," *J. Soc. Indust. Appl. Math.* 11:431–441, Society for Industrial and Applied Mathematics (1963).

Mitsunobu, O., "The Use of Diethyl Azodicarboxylate and Triphenylphosphine in Synthesis and Transformation of Natural Products," *Synthesis* 1:1–28, Georg Thieme Verlag (1981).

Nicosia, R.F., and Madri, J.A., "The Microvascular Extracellular Matrix. Developmental Changes During Angiogenesis in the Aortic Ring–Plasma Clot Model," *Amer. J. Pathol.* 128:78–90, American Association of Pathologists (1987).

Niiya, K., et al., "Increased Surface Expression of the Membrane Glycoprotein IIb/IIIa Complex Induced by Platelet Activation. Relationship to the Binding of Fibrinogen and Platelet Aggregation," *Blood* 70:475–483, Grune & Stratton, Inc. (1987).

Nip, J., et al., "Coordination Expression of the Vitronectin Receptor and the Urokinase–type Plasminogen Activator Receptor in Metastatic Melanoma Cells," *J. Clin. Invest.* 95:2096–2103, The American Society for Clinical Investigation, Inc. (1995).

Okada, Y., et al., "Integrin α$_v$β$_3$ Is Expressed in Selected Microvessels after Focal Cerebral Ischemia," *Amer. J. Pathol.* 149:37–44, American Society for Investigative Pathology (1996).

Relton, J.K., et al., "Inhibition of α4 Integrin Protects Against Transient Focal Cerebral Ischemia in Normotensive and Hypertensive Rats," *Stroke* 32:199–205, American Heart Association, Inc. (Jan. 2001).

Ruoslahti, E., and Giancotti, F.G., "Integrins and Tumor Cell Dissemination," *Cancer Cells* 1:119–126, Cold Spring Harbor Laboratory Press (1989).

Ruoslahti, E., and Reed, J.C., "Anchorage Dependence, Integrenis, and Apoptosis," *Cell* 77:477–478, Cell Press (1994).

Savelon, L., et al., "Substituted pyrido[3,2–b]oxazin–3 (4H)–ones: synthesis and evaluation of antinoceptive activity," *Bioorganic Med. Chem.* 6:133–142, Elsevier Science Ltd. (1998).

Sato, M., et al., "Echistatin Is a Potent Inhibitor of Bone Resorption in Culture," *J. Cell Biol.* 111:1713–1723, The Rockefeller University Press (1990).

Shattil, S.J., "Function and Regulation of the $B_3$ Integrins in Hemostasis and Vascular Biology," *Thromb. Haemost.* 74:149–155, F.K. Schattauer Verlagsgesellschaft mbH (1995).

Topol, E.J., et al., "Randomised trial of coronary intervention with antibody against platelet IIb//IIIa integrin for reduction of clinical restenosis: results at six months," *Lancet 343:*881–886, The Lancet Ltd. (1994).

United States Pharmacopeia/ The National Formulary for 1995, published by United States Pharmacopeial Convention, Inc., Rockville, Maryland, p. 1636 (1994).

White, J.M., "Integrins as virus receptors," *Curr. Biol.* 3:596–599, Current Biology (1993).

Yun, Z., et al., "Involvement of Integrin $\alpha_v\beta_3$ in Cell Adhesion, Motility and Liver Metastasis of Murine RAW117 Large Cell Lymphoma," *Cancer Res.* 56:3103–3111, American Association for Cancer Research (1996).

Carreño, M.C., et al., "N–Bromosuccinimide in Acetonitrile: A Wild and Regiospecific Nuclear Brominating Reagent for Methoxybenzenes and Naphthalenes" *J. Org. Chem.* 60:5328–5331, The American Chemical Society (1995).

Ciattini, P.G., et al., "A New, Palladium–Catalyzed Synthesis of Aromatic Mercapturic Acid Derivatives" *Tetrahedron Lett.* 36:4133–4136, Pergamon Press (1995).

Flynn, B.L., et al., "A Novel Palladium–Mediated Coupling Approach to 2,3–Distributed Benzo [β] thiophenes and Its Application to the Synthesis of Tubulin Binding Agents" *Org. Lett.* 3:651–654, The American Chemical Society (2001).

Fox J.M., et al., "Highly Active and Selective Catalysts for the Formation of α–Aryl Ketones" *J. Am. Chem. Soc.* 122:1360–1370, The American Chemical Society (2000).

Hayashi, T., et al., "Rhodium–Catalyzed Hydroarylation of Alkynes with Arylboronic Acids: 1,4–Shift of Rhodium from 2–Aryl–1–alkenylrhodium to 2–Alkenylarylrhodium Intermediate" *J. Am. Chem. Soc.* 123:9918–9919, The American Chemical Society (2001).

Ishiyama T., et al., "Palladium(0)–Catalyzed Cross–Coupling Reaction of Alkoxydiboron with Haloarenes: A Direct Procedure for Arylboronic Esters" *J. Org. Chem.* 60:7508–7510, The American Chemical Society (1995).

Kim, S., et al., "A Facile Synthesis of 3–Aryl–Substituted–Benzothiophenes via a Lewis Acid Mediated Cyclization of 2–Arylthio–Acetophenones" *Tetrahedron Lett.* 40:2909–2912, Pergamon Press (1999).

Larock, R.C., and Yue, D., "Synthesis of benzo [β] thiophenes by electrophilic cyclization" *Tetrahedron Lett.* 42:6011–6013, Pergamon Press (2001).

Littke, A.F., and Fu, G.C., "Heck Reactions in the Presence of P(t–Bu),:Expanded Scope and Milder Reaction Conditions for the Coupling of Aryl Chlorides" *J. Org. Chem.* 64:10–11, The American Chemical Society (1999).

Littke, A.F., et al., "Versatile Catalysts for the Suzuki Cross–Coupling of Arylboronic Acids with Aryl and Vinyl Halides and Triflates under Mild Conditions" *J. Am. Chem. Soc.* 122: 4020–4028, The American Chemical Society (2000).

Sakuma, S., et al., "Asymmetric Conjugate 1,4–Addition of Arylboronic Acids to α,β–Unsaturated Esters Catalyzed by Rhodium(I) / (S)–binap" *J. Org. Chem.* 65:5951–5955, The American Chemical Society (2000).

Stambuli, J.P., et al., "Screening of Homogeneous Catalysts by Fluorescence Resonance Energy Transfer. Identification of Catalysts for Room–Temperature Heck Reactions" *J. Am. Chem. Soc.* 123:2677–2678, The American Chemical Society (2001).

Venkatraman, S., et al., "Quasi–nature catalysis: conjugated addition of unsaturated carbonyl compounds with aryl and vinyltin reagents catalyzed by rhodium in air and water" *Tetrahedron Lett.* 42:4459–4462, Pergamon Press (2001).

Yue, D., and Larock R.C., "Synthesis of 2,3–Disubstituted Benzo[β]thiophenes via Palladium–Catalyzed Coupling and Electrophilic Cyclization of Terminal Acetylenes" *J. Org. Chem.* 67:1905–1909, The American Chemical Society (2002).

\* cited by examiner

SUBSTITUTED BENZOFURANS AND BENZOTHIOPHENES, METHODS OF MAKING AND METHODS OF USE AS INTEGRIN ANTAGONISTS

This application claims priority to Provisional application 60/324,516, filed on Sep. 26, 2001, and also claims priority to Provisional application 60/286,532, filed on Apr. 27, 2001.

BACKGROUND OF THE INVENTION

1. Field of the Invention

The present invention relates to novel substituted benzofurans and benzothiophenes that are antagonists of alpha V ($\alpha v$) integrins, for example $\alpha_v\beta_3$ and $\alpha_v\beta_5$ integrins, their pharmaceutically acceptable salts, and pharmaceutical compositions thereof.

2. Background Art

Integrins are cell surface glycoprotein receptors which bind extracellular matrix proteins and mediate cell-cell and cell-extracellular matrix interactions (generally referred to as cell adhesion events) (Hynes, R. O., *Cell* 69:11–25 (1992)). These receptors are composed of noncovalently associated alpha ($\alpha$) and beta ($\beta$) chains which combine to give a variety of heterodimeric proteins with distinct cellular and adhesive specificities (Albeda, S. M., *Lab. Invest.* 68:4–14 (1993)). Recent studies have implicated integrins in the regulation of cellular adhesion, migration, invasion, proliferation, apoptosis and gene expression (Albeda, S. M., *Lab. Invest.* 68:4–14 (1993); Juliano, R., *Cancer Met. Rev.* 13:25–30 (1994); Ruoslahti, E. and Reed, J. C., *Cell* 77:477–478 (1994); and Ruoslahti, E. and Giancotti, F. G., *Cancer Cells* 1:119–126 (1989)).

One member of the integrin family which has been shown to play a significant role in a number of pathological conditions is the integrin $\alpha_v\beta_3$, or vitronectin receptor (Brooks, P. C., *DN&P* 10(8):456–461 (1997)). This integrin binds a variety of extracellular matrix components and other ligands, including fibrin, fibrinogen, fibronectin, vitronectin, laminin, thrombospondin, and proteolyzed or denatured collagen (Cheresh, D. A., *Cancer Met. Rev.* 10:3–10 (1991) and Shattil, S. J., *Thromb. Haemost.* 74:149–155 (1995)). The two related $\alpha v$ integrins, $\alpha_v\beta_5$ and $\alpha_v\beta_1$ (also vitronectin receptors), are more specific and bind vitronectin ($\alpha_v\beta_5$) or fibronectin and vitronectin ($\alpha_v\beta_1$) (Horton, M., *Int. J. Exp. Pathol.* 71:741–759 (1990)). $\alpha_v\beta_3$ and the other integrins recognize and bind to their ligands through the tripeptide sequence Arg-Gly-Asp ("RGD") (Cheresh, D. A., *Cancer Met. Rev.* 10:3–10 (1991) and Shattil, S. J., *Thromb. Haemost.* 74:149–155 (1995)) found within all the ligands mentioned above.

The $\alpha_v\beta_3$ integrin has been implicated in a number of pathological processes and conditions, including metastasis and tumor growth, pathological angiogenesis, and restenosis. For example, several studies have clearly implicated $\alpha_v\beta_3$ in the metastatic cascade (Cheresh, D. A., *Cancer Met. Rev.* 10:3–10 (1991); Nip, J. et al., *J. Clin. Invest.* 95:2096–2103 (1995); and Yun, Z., et al., *Cancer Res.* 56:3101–3111 (1996)). Vertically invasive lesions in melanomas are also commonly associated with high levels of $\alpha_v\beta_3$, whereas horizontally growing noninvasive lesions have little if any $\alpha_v\beta_3$ (Albeda, S. M., et al., *Cancer Res.* 50:6757–6764 (1990)). Moreover, Brooks et al. (in *Cell* 79:1157–1164 (1994)) have demonstrated that systemic administration of $\alpha_v\beta_3$ antagonists disrupts ongoing angiogenesis on chick chorioallantoic membrane ("CAM"), leading to the rapid regression of histologically distinct human tumors transplanted onto the CAM. These results indicate that antagonists of $\alpha_v\beta_3$ may provide a therapeutic approach for the treatment of neoplasia (solid tumor growth).

$\alpha_v\beta_3$ has also been implicated in angiogenesis, which is the development of new vessels from preexisting vessels, a process that plays a significant role in a variety of normal and pathological biological events. It has been demonstrated that $\alpha_v\beta_3$ is up-regulated in actively proliferating blood vessels undergoing angiogenesis during wound healing as well as in solid tumor growth. Also, antagonists of $\alpha_v\beta_3$ have been shown to significantly inhibit angiogenesis induced by cytokines and solid tumor fragments (Brooks, P. C., et al., *Science* 264:569–571 (1994); Enenstein, J. and Kramer, R. H., *J. Invest. Dermatol.* 103:381–386 (1994); Gladson, C. L., *J. Neuropathol. Exp. Neurol* 55:1143–1149 (1996); Okada, Y., et al., *Amer. J. Pathol.* 149:37–44 (1996); and Brooks, P. C., et al., *J. Clin. Invest.* 96:1815–1822 (1995)). Such $\alpha_v\beta_3$ antagonists would be useful for treating conditions that are associated with pathological angiogenesis, such as rheumatoid arthritis, diabetic retinopathy, macular degeneration, and psoriasis (Nicosia, R. F. and Madri, J. A., *Amer. J. Pathol.* 128:78–90 (1987); Boudreau, N. and Rabinovitch, M., *Lab. Invest.* 64:187–99 (1991); and Brooks, P. C., *Cancer Met. Rev.* 15:187–194 (1996)).

There is also evidence that $\alpha_v\beta_3$ plays a role in neointimal hyperplasia after angioplasty and restenosis. For example, peptide antagonists and monoclonal antibodies directed to both $\alpha_v\beta_3$ and the platelet receptor $\alpha II_b\beta_3$ have been shown to inhibit neointimal hyperplasia in vivo (Choi, E. T., et al., *J. Vasc. Surg.* 19:125–134 (1994); and Topol, E. J., et al., *Lancet* 343:881–886 (1994)), and recent clinical trials with a monoclonal antibody directed to both $\alpha II_b\beta_3$ and $\alpha_v\beta_3$ have resulted in significant reduction in restenosis, providing clinical evidence of the therapeutic utility of $\beta 3$ antagonists (Topol, E. J., et al., *Lancet* 343:881–886 (1994)).

It has also been reported that $\alpha_v\beta_3$ is the major integrin on osteoclasts responsible for attachment to bone. Osteoclasts cause bone resorption. When bone resorbing activity exceeds bone forming activity, the result is osteoporosis, a condition which leads to an increased number of bone fractures, incapacitation and increased mortality. Antagonists of $\alpha_v\beta_3$ have been shown to be potent antagonists of osteoclastic activity both in vitro (Sato, M., et al., *J. Cell Biol.* 111:1713–1723 (1990)) and in vivo (Fisher, J. E., et al., *Endocrinology* 132:1411–1413 (1993)).

Lastly, White (in *Current Biology* 3(9):596–599 (1993)) has reported that adenovirus uses $\alpha_v\beta_3$ for entering host cells. The $\alpha_v\beta_3$ integrin appears to be required for endocytosis of the virus particle and may be required for penetration of the viral genome into the host cell cytoplasm. Thus, compounds which inhibit $\alpha_v\beta_3$ could be useful as antiviral agents.

The $\alpha_v\beta_5$ integrin has been implicated in pathological processes as well. Friedlander et al. have demonstrated that a monoclonal antibody for $\alpha_v\beta_5$ can inhibit VEGF-induced angiogenesis in rabbit cornea and chick chorioalloantoic membrane, indicating that the $\alpha_v\beta_5$ integrin plays a role in mediating growth factor-induced angiogenesis (Friedlander, M. C., et al., *Science* 270:1500–1502 (1995)). Compounds that act as $\alpha_v\beta_5$ antagonists could be used to inhibit pathological angiogenesis in tissues of the body, including ocular tissue undergoing neovascularization, inflamed tissue, solid tumors, metastases, or tissues undergoing restenosis.

Discovery of the involvement of $\alpha_v\beta_3$ and $\alpha_v\beta_5$ in such processes and pathological conditions has led to an interest in these integrins as potential therapeutic targets, as suggested above. A number of specific antagonists of $\alpha_v\beta_3$ and $\alpha_v\beta_5$ that can block the activity of these integrins have been developed. One major group of such antagonists includes nonpeptide mimetics and organic-type compounds. For example, a number of organic non-peptidic mimetics have been developed that appear to inhibit tumor cell adhesion to a number of $\alpha_v\beta_3$ ligands, including vitronectin, fibronectin, and fibrinogen (Greenspoon, N., et al., *Biochemistry* 32:1001–1008 (1993); Ku, T. W., et al., *J. Amer. Chem. Soc.* 115:8861–8862 (1993); Hershkoviz, R., et al., *Clin. Exp. Immunol.* 95:270–276 (1994); and Hardan, L., et al., *Int. J. Cancer* 55:1023–1028 (1993)).

Additional organic compounds developed specifically as $\alpha_v\beta_3$ or $\alpha_v\beta_5$ integrin antagonists or as compounds useful in the treatment of $\alpha v$-mediated conditions have been described in several recent publications.

For example, U.S. Pat. No. 5,741,796, issued Apr. 21, 1998, discloses pyridyl and naphthyridyl compounds for inhibiting osteoclast-mediated bone resorption.

PCT Published Application WO 97/45137, published Oct. 9, 1997, discloses non-peptide sulfotyrosine derivatives, as well as cyclopeptides, fusion proteins, and monoclonal antibodies, that are useful as antagonists of $\alpha_v\beta_3$ integrin-mediated angiogenesis.

PCT Published Application WO 97/36859, published Oct. 9, 1997, discloses para-substituted phenylpropanoic acid derivatives. The publication also discloses the use of the compounds as $\alpha_v\beta_3$ integrin antagonists.

PCT Published Application WO 97/06791, published February 1997, discloses methods for inhibition of angiogenesis in tissue using vitronectin $\alpha_v\beta_5$ antagonists.

More recently, PCT Published Application WO 97/23451, published Jul. 3, 1997, discloses tyrosine derivatives that are $\alpha v$-integrin antagonists (especially $\alpha_v\beta_3$ antagonists) useful in the treatment of tumors, osteoporoses, and osteolytic disorders and for suppressing angiogenesis.

PCT Published Application WO 98/00395, published Jan. 8, 1998, discloses novel tyrosine and phenylalanine derivatives as $\alpha v$ integrin and GPIIb/IIIa antagonists.

The publication discloses the use of the compounds in pharmaceutical preparations for the treatment of thrombosis, infarction, coronary heart disease, tumors, arteriosclerosis, infection and inflammation.

PCT Published Application WO 99/30713, published Jun. 24, 1999, discloses carboxylic acid derivatives having a cyclic core structure. The derivatives are described as integrin antagonists useful for inhibiting bone resorption, treating and preventing osteoporosis, and inhibiting vascular restenosis, diabetic retinopathy, macular degeneration, angiogenesis, atherosclerosis, inflammation, wound healing, viral disease, tumor growth, and metastasis.

U.S. Pat. No. 6,066,648, issued May 23, 2000, discloses carboxylic acid derivatives of compounds having a 5-membered aromatic or nonaromatic mono- or bicyclic ring system having one heteroatom. The compounds are described as antagonists of the vitronectin receptors and are useful for inhibiting bone resorption, treating and preventing osteoporosis, and inhibiting vascular restenosis, diabetic retinopathy, macular degeneration, angiogenesis, atherosclerosis, inflammation, viral disease, and tumor growth.

PCT Published Application WO 2000/02874, published Jan. 20, 2000, discloses benzofuran derivatives that are integrin antagonists useful in the treatment of a variety of integrin-mediated disease states.

A need continues to exist for non-peptide compounds that are potent and selective integrin antagonists, and which possess greater bioavailability or fewer side-effects than currently available integrin antagonists.

BRIEF SUMMARY OF THE INVENTION

The present invention is directed to substituted benzofurans and benzothiophenes having Formula I (below).

Also provided is a process for preparing compounds of Formula I.

The novel compounds of the present invention exhibit inhibition of $\alpha_v\beta_3$ and $\alpha_v\beta_5$ integrin receptor binding. Also provided is a method of treating $\alpha_v\beta_3$ integrin- and $\alpha_v\beta_5$ integrin-mediated pathological conditions such as tumor growth, metastasis, osteoporosis, restenosis, inflammation, macular degeneration, diabetic retinopathy, and rheumatoid arthritis in a mammal in need of such treatment comprising administering to said mammal an effective amount of a compound of Formula I.

Further provided is a pharmaceutical composition comprising a compound of Formula I and one or more pharmaceutically acceptable carriers or diluents.

DETAILED DESCRIPTION OF THE INVENTION

The present invention is directed to compounds of Formula I:

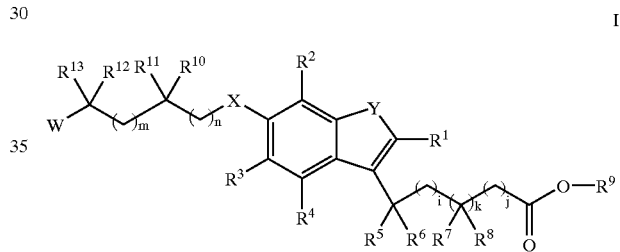

and pharmaceutically acceptable salts thereof; wherein
$R^1$ represents hydrogen, alkyl, haloalkyl, aryl or aralkyl;
$R^2$, $R^3$ and $R^4$ independently represent hydrogen, alkyl, haloalkyl, aryl or aralkyl;
Y is oxygen or sulfur;
$R^5$, $R^6$, $R^7$ and $R^8$ independently represent: hydrogen; hydroxy; alkyl; haloalkyl; alkoxy; haloalkoxy; cycloalkyl; aryl; or heterocycle having 5–14 ring members, optionally substituted with one or more of halogen, hydroxy, cyano, alkyl, haloalkyl, alkoxy, aryl or arylalkyl, arylalkoxy, aryloxy, alkylsulfonyl, alkylsulfinyl, alkylalkoxyaryl, mono- or di-alkylamino, aminoalkyl, monoalkylaminoalkyl, dialkylaminoalkyl, alkanoyl, carboxyalkyl; further wherein: aryl or the aryl group of any aryl-containing moiety may be optionally substituted by one or more of: halogen, hydroxy, cyano, alkyl, aryl, alkoxy, haloalkyl, arylalkyl, arylalkoxy, aryloxy, alkylsulfonyl, alkylsulfinyl, alkylalkoxyaryl, mono- or di-alkylamino, aminoalkyl, monoalkylaminoalkyl, dialkylaminoalkyl, alkanoyl, carboxyalkyl;
or $R^5$ and $R^7$ are taken together to form —$(CH_2)_s$—, wherein s is 0 (a bond) or 1 to 4, while $R^6$ and $R^8$ are defined as above; or $R^{10}$ and $R^{11}$ are taken together to form —$(CH_2)_t$—, wherein t is 2 to 8, while $R^5$ and $R^7$ are defined as above; or $R^7$ and $R^8$ are taken together to form —$(CH_2)_u$— wherein u is 2 to 8, while $R^5$ and $R^6$ are defined as above;
i is from 0 to 4;

j is from 0 to 4; and
k is 0 or 1;
R⁹ is hydrogen or a functionality which acts as a prodrug (i.e., converts to the active species by an endogenous biological process such as an esterase, lipase, or other hydrolase), such as alkyl, haloalkyl, aryl, aralkyl, dialkylaminoalkyl, 1-morpholinoalkyl, 1-piperidinylalkyl, pyridinylalkyl, alkoxy(alkoxy)alkoxyalkyl, or (alkoxycarbonyl)oxyethyl;

R¹⁰, R¹¹, R¹² and R¹³ independently represent hydrogen, alkyl, haloalkyl, hydroxyalkyl, aminoalkyl, monoalkylaminoalkyl, dialkylaminoalkyl, carboxyalkyl, aryl or aralkyl;

or R¹⁰ and R¹¹ are taken together to form —(CH₂)$_p$—, where p is 2–8, while R¹² and R¹³ are defined as above; or R¹² and R¹³ are taken together to form —(CH₂)$_q$—, where q is 2–8, while R¹⁰ and R¹¹ are defined as above; or R¹⁰ and R¹² are taken together to form —(CH₂)$_r$—, while r is zero (a bond), 1 or 2, while R₁₁ and R¹³ are defined as above;

X represents oxygen, sulfur, CH₂ or NH;
n is from 0 to 4;
m is from 0 to 4;
W is:

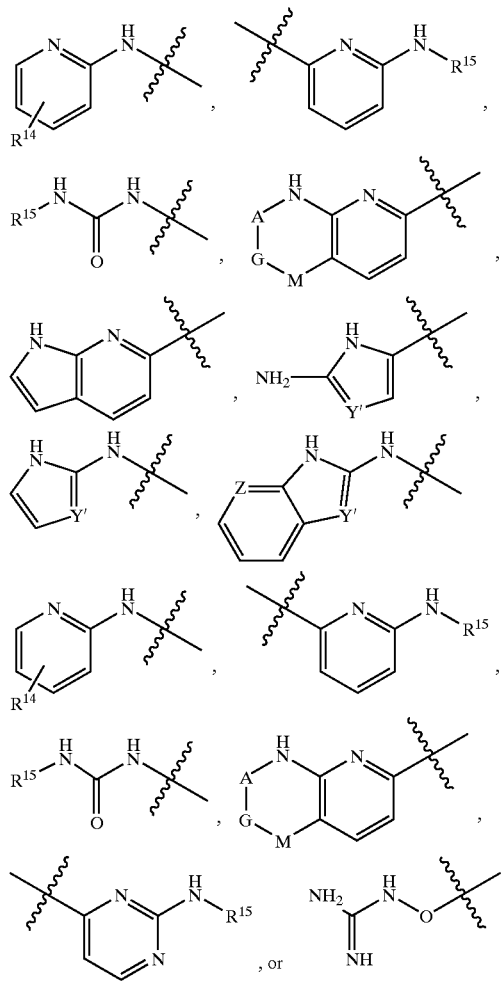

wherein:
A, G and M are independently oxygen, sulfur, CH₂, CH—R$^a$, C(R$^a$)(R$^b$), NH or N—R$^a$, wherein R$^a$ and R$^b$ are independently selected from alkyl, haloalkyl or aryl;
Y' is NH, sulfur or CH;

Z is N or CH;
R¹⁵ is hydrogen, alkyl, haloalkyl, aryl or arylalkyl; and
R¹⁴ is hydrogen, alkyl, haloalkyl or halogen.

When any variable occurs more than one time in any constituent or in Formula I, its definition on each occurrence is independent of its definition at every other occurrence. Also, combinations of substituents and/or variables are permissible only if such combinations result in stable compounds.

The term "alkyl" as employed herein by itself or as part of another group refers to both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl. Alkyl having from 1–6 carbon atoms is more preferred; and alkyl having from 1–4 carbons is most preferred.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length. Alkoxy from 1–4 carbon atoms is most preferred.

The term "aryl" as employed herein by itself or as part of another group refers to monocyclic or bicyclic aromatic groups containing from 6 to 14 carbons in the ring portion, preferably 6–10 carbons in the ring portion, such as phenyl, naphthyl or tetrahydronaphthyl.

The term "aryloxy" as employed herein by itself or as part of another group refers to monocyclic or bicyclic aromatic groups containing from 6 to 14 carbons in the ring portion, preferably 6–10 carbons in the ring portion, bonded to an oxygen atom. Examples include, but are not limited to, phenoxy, naphthoxy, and the like.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, benzofuranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perirnidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to C$_{1-6}$alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "heterocycle" or "heterocyclyl" as used herein, except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, chromanyl, benzimidazolyl, thiadiazoyl, benzopyranyl, benzothiazolyl, benzo[b]thiophenyl, benzo[2,3-c]1,2,5-oxadiazolyl, benzoxazolyl, benzodioxolyl, furanyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "halogen" or "halo" as employed herein by itself or as part of another group (e.g., haloalkyl) refers to chlorine, bromine, fluorine or iodine with chlorine or fluorine being preferred.

The term "monoalkylamino" as employed herein by itself or as part of another group refers to an amino group which is substituted with one alkyl group, preferably having from 1 to 6 carbon atoms.

The term "dialkylamino" as employed herein by itself or as part of another group refers to an amino group which is substituted with two alkyl groups, each perferably having from 1 to 6 carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "haloalkyl" as employed herein refers to any of the above alkyl groups substituted by one or more chlorine, bromine, fluorine or iodine with fluorine and chlorine being preferred, such as chloromethyl, iodomethyl, trifluoromethyl, 2,2,2-trifluoroethyl, and 2-chloroethyl.

The term "haloalkoxy" as used herein refers to any of the above haloalkyl groups bonded to an oxygen atom, such as trifluromethoxy, trichloromethoxy, and the like.

Preferred compounds of the present invention are those of Formula I, wherein $R^1$ represents hydrogen, $C_{1-6}$alkyl, $C_{1-6}$haloalkyl, $C_{6-10}$aryl, or $C_{6-10}$ar($C_{1-6}$)alkyl, preferably hydrogen, methyl, ethyl, propyl, butyl, fluoromethyl, fluoroethyl, fluoropropyl, fluorobutyl phenyl, benzyl or phenylethyl.

Also preferred are compounds of Formula I, wherein $R^2$, $R^3$ and $R^4$ independently represent hydrogen, $C_{1-6}$alkyl, $C_{1-6}$haloalkyl, $C_{6-10}$aryl, or $C_{6-10}$ar($C_{1-6}$)alkyl, preferably, $R^2$, $R^3$ and $R^4$ are hydrogen, $C_{1-4}$alkyl or $C_{1-4}$fluoroalkyl.

Preferred compounds are those of Formula I, wherein $R^{10}$, $R^{11}$, $R^{12}$ and $R^{13}$ independently represent hydrogen, $C_{1-4}$alkyl or $C_{1-4}$fluoroalkyl.

Preferred compounds are those of Formula I, wherein X is oxygen or $CH_2$.

Also preferred are compounds of Formula I, wherein W is

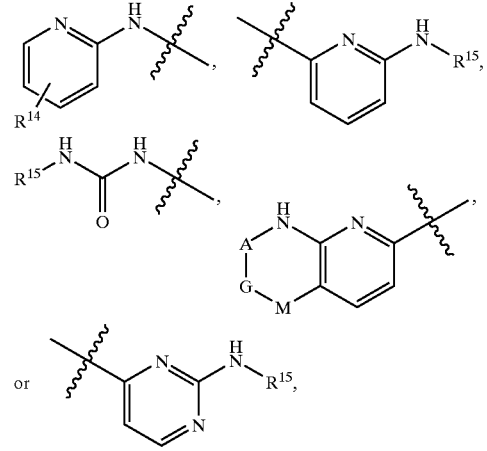

wherein
$R^{15}$ is hydrogen, $C_{1-6}$alkyl or $C_{6-10}$ar($C_{1-6}$)alkyl;
$R^{14}$ is hydrogen or $C_{1-4}$alkyl;
A and G are independently selected from $CH_2$, CH—$R^a$ or C($R^a$)($R^b$), wherein $R^a$ and $R^b$, are independently selected from alkyl, haloalkyl or aryl; and
M is selected from $CH_2$, CH—$R^a$ or C($R^a$)($R^b$), wherein $R^a$ and $R^b$, are as defined above, or oxygen.

Further preferred compounds are those of Formula I, wherein $R^5$, $R^6$, $R^7$ and $R^8$ independently represent: hydrogen; hydroxy; $C_{1-6}$alkyl; $C_{1-6}$haloalkyl; $C_{1-6}$alkoxy; $C_{1-6}$haloalkoxy; $C_{3-7}$cycloalkyl; $C_{6-14}$aryl; or quinolyl, benzofuranyl, benzodioxolyl, or pyridyl, each of which are optionally substituted with one or more of halogen, hydroxy, cyano, $C_{1-6}$alkyl, $C_{1-6}$haloalkyl, $C_{1-6}$alkoxy, $C_{6-14}$aryl or $C_{6-14}$aryl($C_{1-6}$)alkyl, $C_{6-14}$aryl($C_{1-6}$)alkoxy, $C_{6-14}$aryloxy, $C_{1-6}$alkylsulfonyl, $C_{1-6}$alkylsulfinyl, $C_{1-6}$alkyl($C_{1-6}$)alkoxy ($C_{6-14}$)aryl, mono- or di-($C_{1-6}$)alkylamino, amino($C_{1-6}$) alkyl, mono($C_{1-6}$)alkylamino($C_{1-6}$)alkyl, di($C_{1-6}$) alkylamino($C_{1-6}$)alkyl, $C_{1-6}$alkanoyl, carboxy($C_{1-6}$)alkyl; further wherein: aryl or the aryl group of any aryl-containing moiety may be optionally substituted by one or more of: halogen, hydroxy, cyano, $C_{1-6}$alkyl, $C_{6-14}$aryl, $C_{1-6}$alkoxy, $C_{1-6}$haloalkyl, $C_{6-14}$aryl($C_{1-6}$)alkyl, $C_{6-14}$aryl($C_{1-6}$)alkoxy, $C_{6-14}$aryloxy, $C_{1-6}$alkylsulfonyl, $C_{1-6}$alkylsulfinyl, ($C_{1-6}$) alkylalkoxy($C_{6-14}$)aryl, mono- or di-($C_{1-6}$)alkylamino, amino($C_{1-6}$)alkyl, mono($C_{1-6}$)alkylamino($C_{1-6}$)alkyl, di-($C_{1-6}$)alkylamino($C_{1-6}$)alkyl, alkanoyl, or carboxy($C_{1-6}$) alkyl.

Preferred compounds of the present invention are also those wherein one of $R^5$ and $R^6$ is hydrogen, and the other is selected from: quinol-3-yl; benzofuran-6-yl; benzodioxol-5-yl; or pyrid-3-yl, each of which may be optionally substituted with one or more of halogen, hydroxy, cyano, $C_{1-6}$alkyl, $C_{1-6}$haloalkyl, $C_{1-6}$alkoxy, $C_{6-14}$aryl or $C_{6-14}$aryl ($C_{1-6}$)alkyl, $C_{6-14}$aryl($C_{1-6}$)alkoxy, $C_{6-14}$aryloxy, $C_{1-6}$alkylsulfonyl, $C_{1-6}$alkylsulfinyl, $C_{1-6}$alkyl($C_{1-6}$)alkoxy ($C_{6-14}$)aryl, mono- or di-($C_{1-6}$)alkylamino, amino($C_{1-6}$) alkyl, mono($C_{1-6}$)alkylamino($C_{1-6}$)alkyl, di($C_{1-6}$) alkylamino($C_{1-6}$)alkyl, $C_{1-6}$alkanoyl, carboxy($C_{1-6}$)alkyl;

further wherein: aryl or the aryl group of any aryl-containing moiety may be optionally substituted by one or more of: halogen, hydroxy, cyano, $C_{1-6}$alkyl, $C_{6-14}$aryl, $C_{1-6}$alkoxy, $C_{1-6}$haloalkyl, $C_{6-14}$aryl($C_{1-6}$)alkyl, $C_{6-14}$aryl($C_{1-6}$)alkoxy, $C_{6-14}$aryloxy, $C_{1-6}$alkylsulfonyl, $C_{1-6}$alkylsulfinyl, ($C_{1-6}$) alkylalkoxy($C_{6-14}$)aryl, mono- or di-($C_{1-6}$)alkylamino, amino($C_{1-6}$)alkyl, mono($C_{1-6}$)alkylamino($C_{1-6}$)alkyl, di-($C_{1-6}$)alkylamino($C_{1-6}$)alkyl, alkanoyl, or carboxy($C_{1-6}$) alkyl.

Additionally preferred compounds according to this aspect of the invention are those wherein one of $R^5$ and $R^6$ is hydrogen, and the other is pyrid-3-yl, which is optionally substituted with aryl, wherein the aryl is phenyl, and the phenyl is optionally substituted by one or more of: halogen, hydroxy, cyano, $C_{1-6}$alkyl, $C_{6-14}$aryl, $C_{1-6}$alkoxy, $C_{1-6}$haloalkyl, $C_{6-14}$aryl($C_{1-6}$)alkyl, $C_{6-14}$aryl($C_{1-6}$)alkoxy, $C_{6-14}$aryloxy, $C_{1-6}$alkylsulfonyl, $C_{1-6}$alkylsulfinyl, ($C_{1-6}$) alkylalkoxy($C_{6-14}$)aryl, mono- or di-($C_{1-6}$)alkylamino, amino($C_{1-6}$)alkyl, mono($C_{1-6}$)alkylamino($C_{1-6}$)alkyl, di-($C_{1-6}$)alkylamino($C_{1-6}$)alkyl, alkanoyl, or carboxy($C_{1-6}$) alkyl.

Also preferred are those compounds of Formula I, wherein $R^5$ and $R^7$ are taken together to form —(CH$_2$)$_s$— where s is zero or 1 to 4, and $R^6$ and $R^8$ are each hydrogen.

Preferred compounds are those of Formula I, wherein $R^5$ and $R^6$ are taken together to form —(CH$_2$)$_t$, where t is 2 to 5 and $R^7$ and $R^8$ are each hydrogen.

Further preferred compounds are those of Formula I, wherein i and j are 0.

Preferred compounds are those of Formula I, wherein k is 1.

Also preferred compounds are those of Formula I, wherein $R^9$ is hydrogen.

Preferred compounds are those of Formula I, wherein i and j are each zero; k is one; $R^5$, $R^6$ and $R^7$ are each hydrogen; and $R^8$ is hydrogen, $C_{1-6}$alkyl, $C_{1-6}$haloalkyl, $C_{6-10}$aryl or $C_{6-10}$ar($C_{1-4}$)alkyl.

Preferred compounds of the present invention are those of Formula I wherein:

$R^1$ is hydrogen, $C_{1-4}$alkyl or $C_{1-6}$haloalkyl, more preferably, hydrogen, methyl or fluoromethyl;

$R^2$, $R^3$, and $R^4$ are hydrogen, $C_{1-4}$alkyl or $C_{1-6}$haloalkyl, more preferably hydrogen, methyl or fluoromethyl;

$R^{10}$, $R^{11}$, $R^{12}$ and $R^{13}$ are preferably hydrogen, $C_{1-4}$alkyl or $C_{1-6}$haloalkyl, more preferably, hydrogen, methyl or fluoromethyl;

X is oxygen or CH$_2$;
n is 0 or 1;
m is 0 or 1;
$R^5$, $R^6$, $R^7$ and $R^8$ independently represent hydrogen, $C_{1-6}$alkyl, $C_{1-6}$haloalkyl or $C_{6-10}$ar($C_{1-6}$)alkyl;
or one of the combination $R^5$ or $R^6$, $R^7$ or $R^8$, $R^5$ and $R^7$ are taken together to form —(CH$_2$)$_s$—, wherein s is 1 or 2 while the remaining $R^5$–$R^8$ are defined above;
i is 0 or 1;
j is 0 or 1;
k is 0 or 1;
$R^9$ is hydrogen, $C_{1-6}$alkyl or benzyl;
W is:

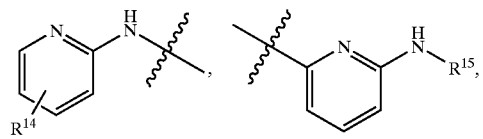

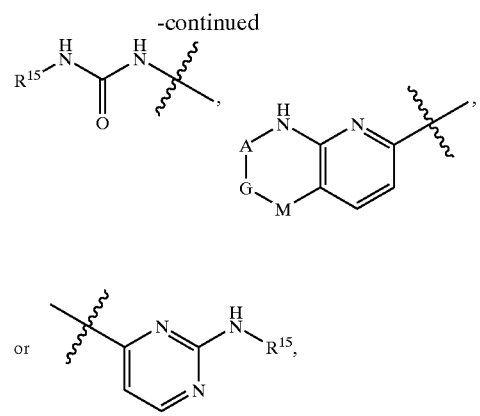

wherein
$R^{15}$ is hydrogen, $C_{1-6}$alkyl, $C_{1-6}$haloalkyl or $C_{6-10}$ar-($C_{1-6}$)alkyl such as benzyl;
$R^{14}$ is hydrogen, $C_{1-4}$alkyl or $C_{1-4}$haloalkyl; and
A and G are independently selected from CH$_2$, CH—$R^a$ or C($R^a$)($R^b$), wherein $R^a$ and $R^b$, are independently selected from $C_{1-6}$alkyl, $C_{1-6}$haloalkyl or $C_{6-10}$aryl; and
M is selected from CH$_2$, CH—$R^a$ or C($R^a$)($R^b$) or oxygen, wherein $R^a$ and $R^b$ are as defined above.

Preferred compounds of the present invention include:
3-(6-{2-[6-methylamino)-2-pyridyl]ethoxy}benzo[b] thiophen-3-yl)propanoic acid;
3-(6-{2-[6-(methylamino)-2-pyridyl]ethoxy}benzo[b] furan-3-yl)propanoic acid;
3-quinolin-3-yl-3-{6-[2-(5,6,7,8-tetrahydro-[1,8] naphthyridin-2-yl)-ethoxy]-benzo[b]thiophen-3-yl}-propionic acid;
3-{6-[2-(6-methylamino-pyridin-2-yl)-ethoxy]-benzo[b] thiophen-3-yl}-3-quinolin-3-yl-propionic acid;
3-(2,3-dihydro-benzofuran-6-yl)-3-{6-[2-(5,6,7,8-tetrahydro-[1,8]naphthyridin -2-yl)-ethoxy]-benzo[b] thiophen-3-yl}-propionic acid;
3-(2,3-dihydro-benzofuran-6-yl)-3-{6-[2-(6-methylamino-pyridin-2-yl)-ethoxy ]-benzo[b]thiophen-3-yl}-propionic acid;
3-benzo [1,3]dioxol-5-yl-3-{6-[2-(3,4-dihydro-2H-pyrido[3,2-b][1,4]oxazin-6-yl)-ethoxy]-benzo[b]thiophen-3-yl}-propionic acid;
3-benzo[1,3]dioxol-5-yl-3-{6-[2-(5,6,7,8-tetrahydro-[1, 8]naphthyridin-2-yl)-ethoxy]-benzo[b]thiophen-3-yl}-propionic acid;
3-benzo [1,3]dioxol-5-yl-3-{6-[2-(6-methylamino-pyridin-2-yl)-ethoxy]-benzo[b]thiophen-3-yl}-propionic acid;
3-pyridin-3-yl-3-{6-[2-(5,6,7,8-tetrahydro-[1,8] naphthyridin-2-yl)-ethoxy]-benzo[b]thiophen-3-yl}-propionic acid;
3-(5-phenyl-pyridin-3-yl)-3-{6-[2-(5,6,7,8-tetrahydro-[1, 8]naphthyridin-2-yl)-ethoxy]-benzo[b]thiophen-3-yl}-propionic acid;
3-quinolin-3-yl-3-{6-[2-(5,6,7,8-tetrahydro-[1,8] naphthyridin-2-yl)-ethoxy]-benzofuran-3-yl }-propionic acid;
3-{6-[2(6-methylamino-pyridin-2-yl)-ethoxy]-benzofuran-3-yl }-3-quinolin-3-yl-propionic acid;
3-(2,3-dihydro-benzofuran-6-yl)-3-{6-[2-(5,6,7,8-tetrahydro-[1,8]naphthyridin-2-yl)-ethoxy]-benzofuran-3-yl}-propionic acid;
3-(2,3-dihydro-benzofuran-6-yl)-3-{6-[2-(6-methylamino-pyridin-2-yl)-ethoxy]-benzofuran-3-yl}-propionic acid;

3-benzo[1,3]dioxol-5-yl-3-{6-[2-(3,4-dihydro-2H-pyrido[3,2-b][1,4]oxazin-6-yl)-ethoxy]-benzofuran-3-yl}-propionic acid;

3-benzo[1,3]dioxol-5-yl-3-{6-[2-(5,6,7,8-tetrahydro-[1,8]naphthyridin-2-yl)-ethoxy]-benzofuran-3-yl}-propionic acid;

3-benzo[1,3]dioxol-5-yl-3-{6-[2-(6-methylamino-pyridin-2-yl)-ethoxy]-benzofuran-3-yl}-propionic acid;

3-pyridin-3-yl-3-{6-[2-(5,6,7,8-tetrahydro-[1,8]naphthyridin-2-yl)-ethoxy]-benzofuran-3-yl}-propionic acid; and 3-(5-phenyl-pyridin-3-yl)-3-{6-[2-(5,6,7,8-tetrahydro-[1,8]naphthyridin-2-yl)-ethoxy]-benzofuran-3-yl}-propionic acid;

or a pharmaceutically acceptable salt, hydrate, solvate or prodrug thereof.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The present invention is also directed to method for preparing compounds of Formula I, comprising:

reacting a compound of Formula II:

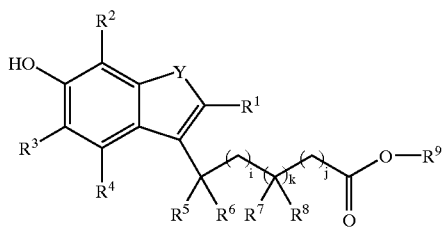

II or a salt, hydrate or solvate thereof, wherein $R^1$, $R^2$, $R^3$, $R^4$, $R^5$, $R^6$, $R^7$, $R^8$, $R^9$, i, j and k are as defined as above, with a compound of Formula III:

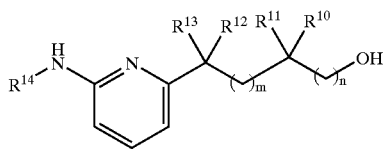

III or a salt, hydrate or solvate thereof, wherein $R^{14}$ is as defined above, to form the compound Formula I.

The present invention is also directed to a method for preparing compounds of Formula I, comprising reacting a compound of Formula II:

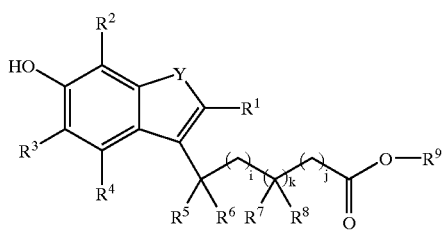

II or a salt, hydrate or solvate thereof, wherein $R^1$, $R^2$, $R^3$, $R^4$, $R^5$, $R^{10}$, $R^{11}$, $R^{12}$, $R^{13}$, $R^{14}$, i, j and k are as defined above, with a compound of Formula IV:

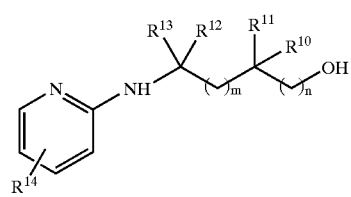

IV or a salt, hydrate or solvate thereof, wherein $R^{10}$, $R^{11}$, $R^{12}$, $R^{13}$, $R^{14}$, m and n are as defined above, to form the compound of Formula I.

The present invention is also directed to a method for preparing compounds of Formula I, comprising reacting a compound of Formula V:

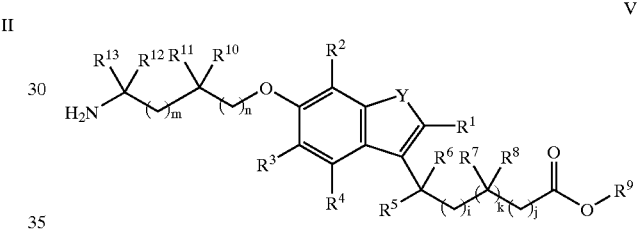

V or a salt, hydrate or solvate thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, i, j, k, m and n are as defined in claim 1, with $R^{15}$NCO, where $R^{15}$ is as defined in claim 1, to form a substituted benzofuran or benzothiophene compound of claim 1.

The compounds of the present invention may be prepared by the general procedures outlined in Schemes I, II and III (below), where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, n, m, i, j, X and W are as defined above.

Additionally, for each of the schemes below, $R_{16}$, $R_{17}$, $R_{18}$, $R_{19}$, $R_{20}$ and $R_{27}$ are independently selected from: hydrogen, $C_{1-6}$alkyl, $C_{1-6}$haloalkyl or $C_{6-10}$aryl.

Schemes Ia, Ib, Ic, Id and Ie outline the synthetic steps to produce the compounds of the present invention.

For each of the schemes depicted below, the R-groups having reference numbers as subscripts are not intended to represent a plurality of said R-group, but rather, distinguish between different R-groups throughout the application. Thus, the subscripted reference numbers on each of the R-groups should be interpreted as though they were superscripts.

Scheme Ia

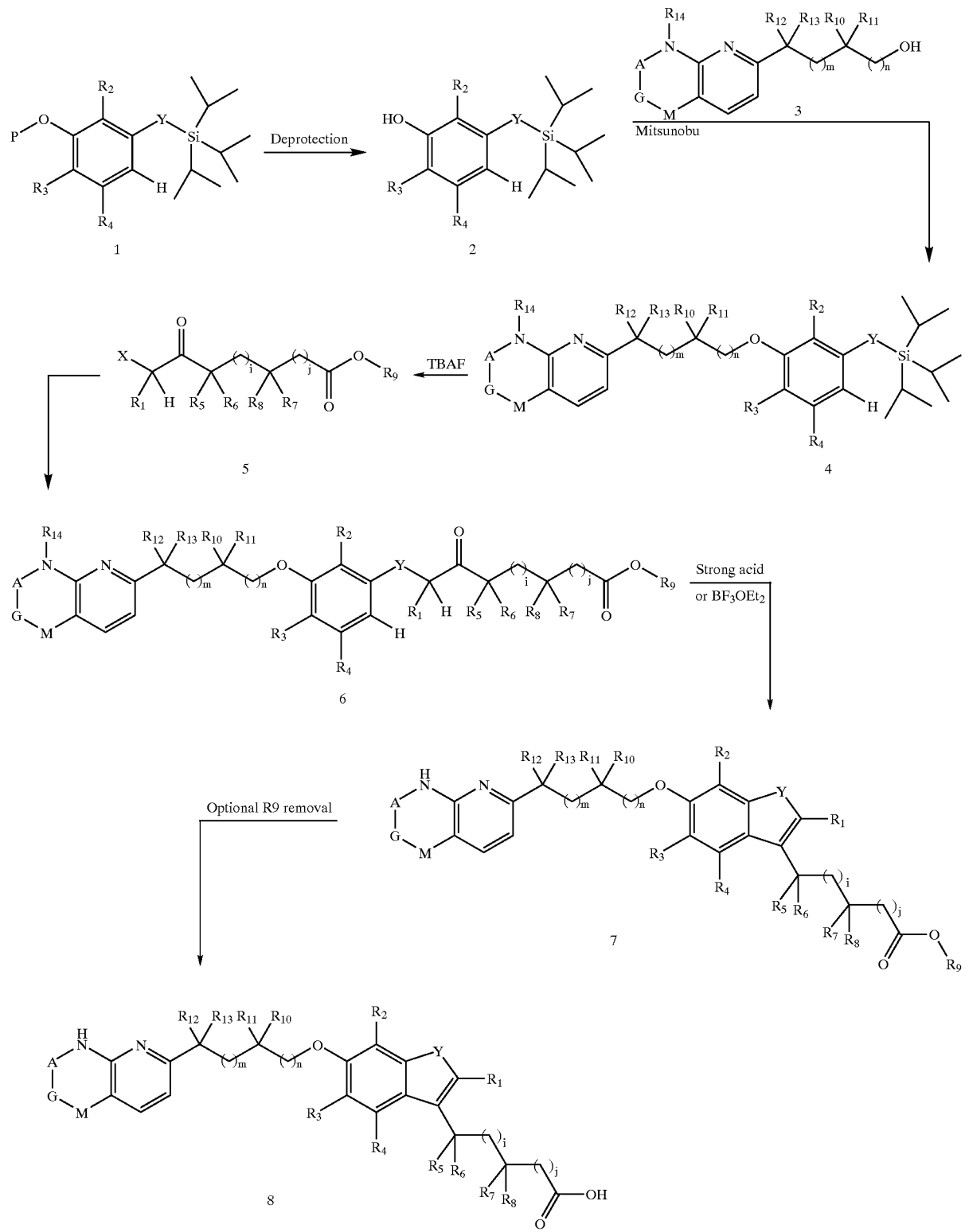

In Scheme Ia, the protected compound 1 (P is a protecting group), such as 3-[1,1-bis(Methylethyl)-2-methyl-1-silapropylthio]phenyl acetate, is deprotected by conditions well known in the art (Greene, T. W. and Wuts, P. G. M., supra). For example, deprotection of acetyl esters may be effected through basic hydrolysis, using aqueous sodium hydroxyde as a base in a suitable solvent, such as methanol or tetrahydrofuran. Phenol 2 is coupled to compound 3 using a Mitsunobu coupling procedure (Mitsunobu, O., *Synthesis*, 1 (1981)) to give compound 4. Preferred coupling conditions include using a trialkylphosphine or triarylphosphine, such as triphenylphosphine or tri-n-butylphosphine, in a suitable solvent, such as tetrahydrofuran or methylene chloride, and an azodicarbonyl reagent, such as diethyl azodicarboxylate, diisopropyl azodicarboxylate or 1,1'-(azodicarbonyl) dipiperidine. Compound 4, [6-(2-{3-[1,1-bis(Methylethyl)-2-methyl-1-silapropylthio]phenoxy}ethyl)(2-pyridyl)]methylamine, is reacted with a β-halogen ketone 5, such as Ethyl 5-bromo-4-oxopentanoate, in a suitable solvent, such a tetrahydrofuran, in the presence of tetrabutylamonium fluoride, to yield compound 6. Formation of the five member pseudoaromatic ring can be accomplished dissolving the compound 6 in a strong acid, such as Sulfuric acid or Polyphophoric acid. The reaction can be performed at a wide range of temperatures, from −5° C. to 120° C., with or without a co-solvent, such a toluene or chlorobenzene. Alternatively, compound 6 can be obtaining using $BF_3OEt_2$ (Kim S. et al., Tethahedron Letters, 40, 1999, 2909–2912). Compound 8 could be obtained via basic hydrolysis of ester 7, using aqueous sodium hydroxide as a base in a suitable solvent, such methanol or tetrahydrofuran.

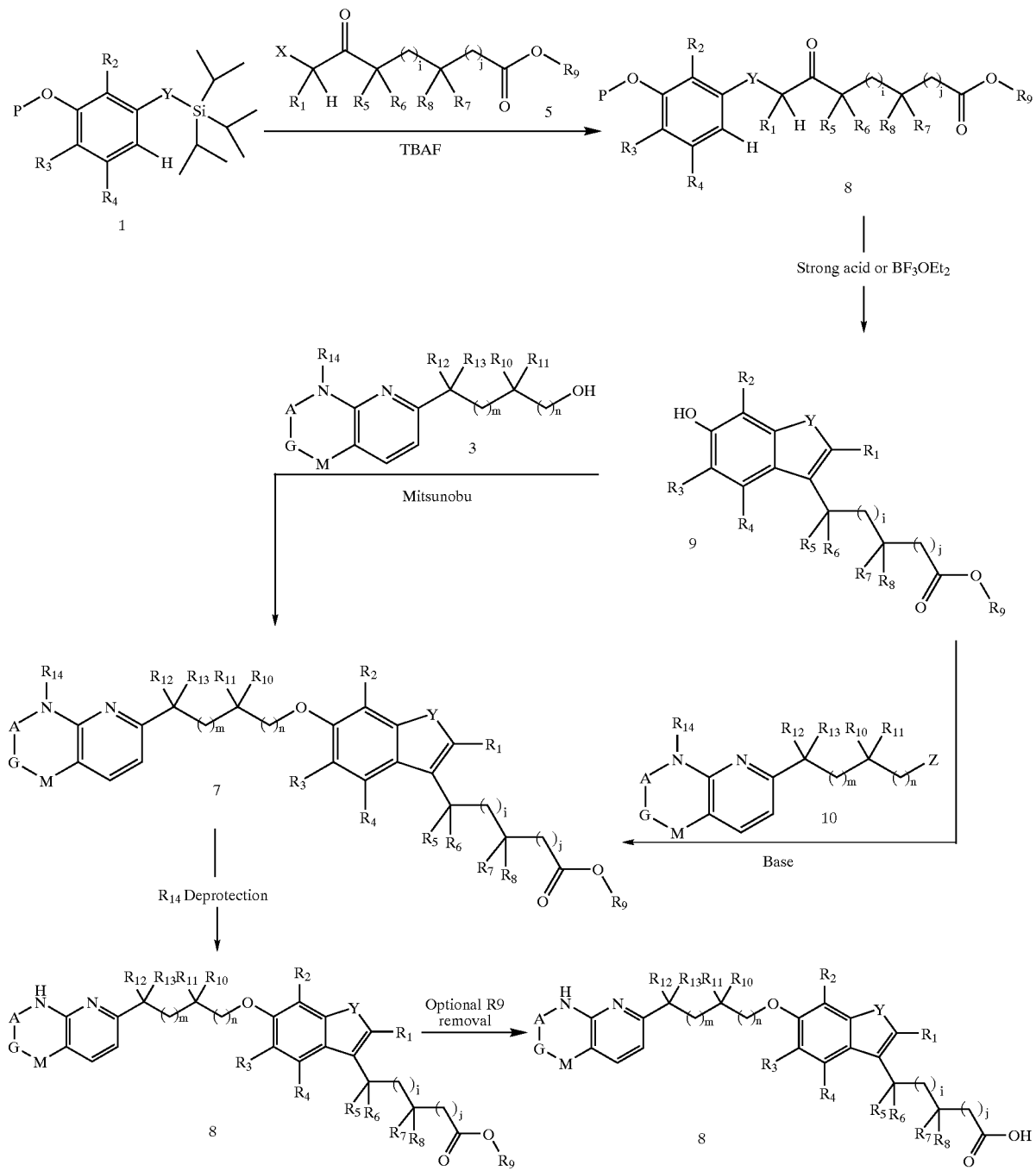

Scheme Ib

In Scheme Ib, compound 1, for example 3-[1,1-bis(Methylethyl)-2-methyl-1-silapropylthio]phenyl acetate, is reacted with a β-halogen ketone 5, such as Ethyl 5-bromo-4-oxopentanoate, in a suitable solvent, such a tetrahydrofuran, in the presence of tetrabutylamonium fluoride, to yield compound 8. Formation of the five member pseudoaromatic ring can be accomplished dissolving the compound 8 in a strong acid, such as sulfuric acid or polyphophoric acid to yield compound 9. The reaction can be performed in a wide range of temperatures, from −5° C. to 120° C., with or without a co-solvent, such a toluene or chlorobenzene. Alternatively, compound 9 can be obtaining using $BF_3OEt2$ (Kim S. et al., Tethahedron Letters, 40, 1999, 2909–2912). Phenol 9 is coupled to the compound 3 using a Mitsunobu coupling procedure (Mitsunobu, O., *Synthesis*, 1 (1981)) to give compound 7. Preferred coupling conditions include using a trialkylphosphine or triarylphosphine, such as triphenylphosphine or tri-n-butylphosphine, in a suitable solvent, such as tetrahydrofuran or methylene chloride, and an azodicarbonyl reagent, such as diethyl azodicarboxylate, diisopropyl azodicarboxylate or 1,1'-(azodicarbonyl)dipiperidine.

It is also possible to alkylate compound 9 using the alkylating agent 10 in the present of an adequate base, such as sodium hydride, in a suitable solvent, such as N,N-dimethylformamide.

The alkylating agent 10 could be synthesized from compound 3, transforming the alcohol to a living group, such as a halogen or methylsulfonate.

Scheme Ic

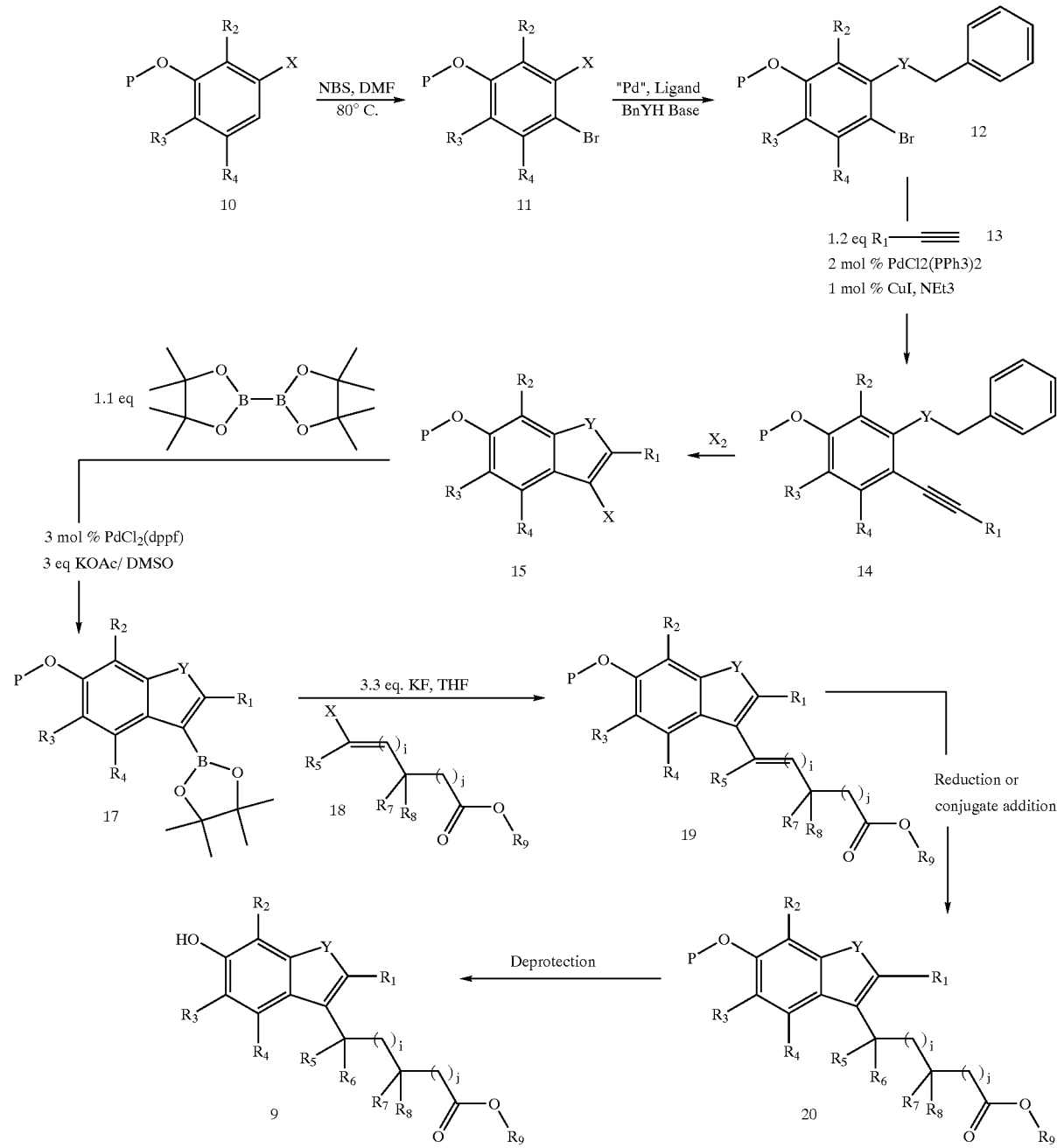

In Scheme Ic, a suitable protected phenol is brominated with N-bromosuccinimide regiospecific fashion (Garcia Ruano, J. L. et al., J. Org. Chem., 1995, 60, 5328–5331) to arrive to compound 11. Then, cross coupling reaction with the proper thiol or alcohol can be accomplished using an adequate palladium catalyst, a suitable ligand and a base to obtain compound 12. In the case of the thiol, preferred coupling conditions are tris(dibenzylideneacetone) dipalladium (0) as calatyst, 1,1'-Bis(diphenylphosphino) ferrocene as ligand, triethylamine as base and N-N-dimethylformamide as solvent (Ortar, G. et al, Tetrahedron Letters, 1995, 36(23), 4133–4136). In the case of the alcohol, preferred coupling conditions are Palladium (II) acetate as calatyst, [1,1']Binaphthalenyl-2-yl-di-tert-butyl-phosphane as ligand, and cesium carbonate as base (Stephen Buchwald, personal communication). Compound 12 can be reacted in an other cross-coupling type reaction, this time with a terminal acetylene 13. Preferred coupling conditions are dichlorobis(triphenylphosphine)palladium (II) as calatyst, copper (I) idodide as co-catalyst, and triethylarnine as base (Larock, R. C. et al, J. Org. Chem., 2002, 67, 1905–1909). A range of electrophiles can accomplish cyclization of compound 14. Preferred conditions are iodine, bromine or N-bromosuccinimide (Larock, R. C. et al, Tetrahedron Letters, 2001, 42, 6011–6013; Larock, R. C. et al, J. Org. Chem., 2002, 67, 1905–1909; Flynn B. L. et al., Organic Letters, 2001, 3(5), 651–654). Introduction of the boronic ester can be done reacting the compound 15 with 4,4,5,5,4',4',5',5'-Octamethyl-[2,2']bi[[1,3,2] dioxaborolanyl] 16. Preferred coupling conditions are dichloro[1,1'-bis(diphenylphosphino)ferrocene]palladium (II) as calatyst, potassium acetate as base and dimetylsul-foxide as solvent (Miyaura N. et al., J. Org. Chem., 1995, 60, 7508–7510). Compound 17 can be coupling with a suitable vinyl halide 18 to yield compound 19. Preferred coupling conditions are tris(dibenzylideneacetone)dipalladium (0) as calatyst, tri-t-butylphosphine as ligand, potassium fluoride as base and tetrahydrofuran as solvent (Fu G. C. et al., J. Am. Chem. Soc., 2000, 122, 4020–4028). Compound 19 can be transformed to compound 20 via reduction or conjugate addition to the double bond. Preferred reduction conditions are palladium (0) on activated carbon as catalyst under hydrogen atmosphere and methanol as solvent. In the case of the conjugate addition, preferred conditions are acetylacetonatebis(1,5-cylooctadiene)rhodium (I) as catalyst, in the presence of a suitable alkyl or aryl boronic acid or ester and 2,2'-Bis(diphenylphosphino)-1,1'-binaphtyl (Miyaura N. et al., J. Org. Chem., 2000, 65, 5951–5955) or in the presence of an organotin reagent (Li, C-J. et al, Tetrahedron Letters, 2001, 42, 4459–4462). Compound 19 can be deprotected to yield compound 20. When the protecting group is a methyl, preferred deprotection conditions are borotribromide in methylene choride. Compound 9 can be transformed to final compound following schemes Ia and Ib.

Scheme Id

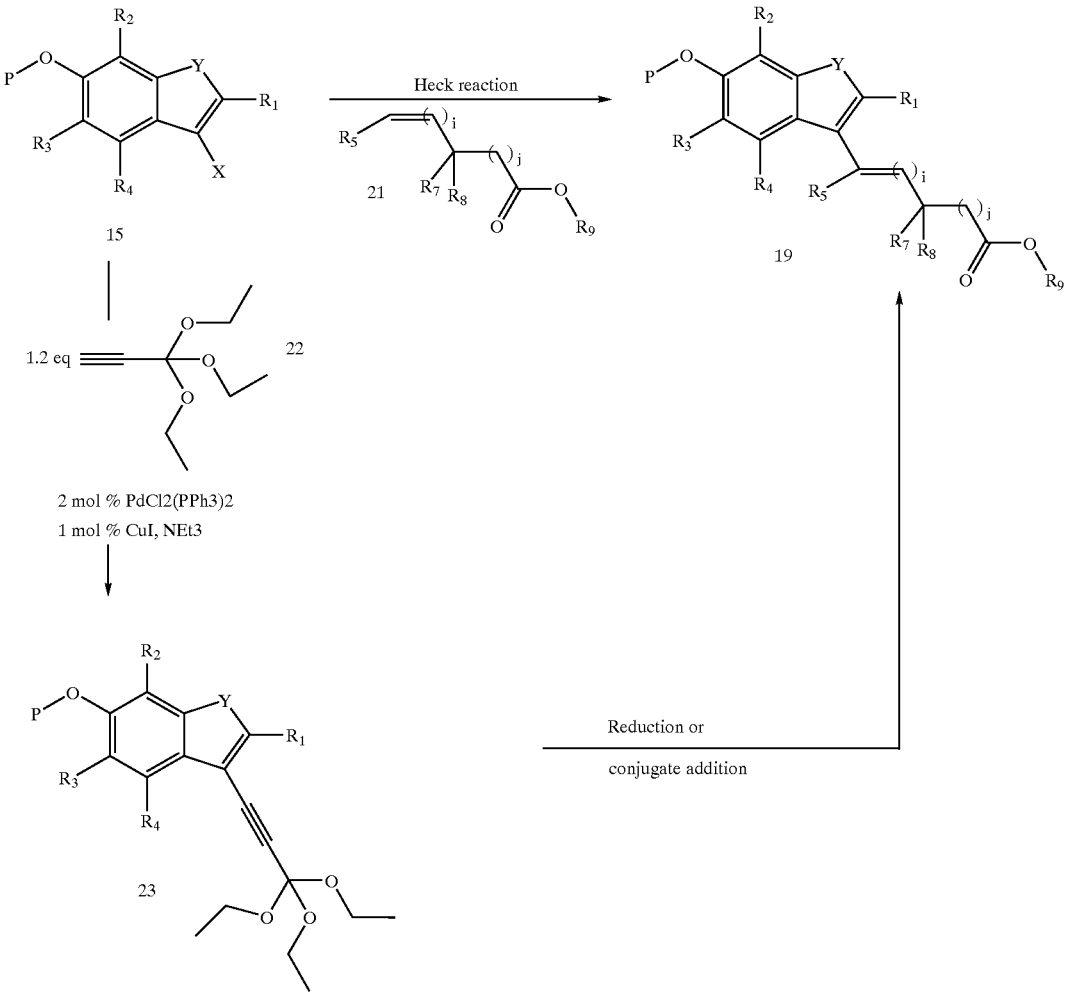

In Scheme Id, Compound 15 can be reacted with an alkene 21 to yield compound 19 using a Heck reaction. Preferred coupling conditions are tris(dibenzylideneacetone)dipalladium (0) as calatyst, tri-t-butylphosphine as ligand, cesium carbonate as base and dioxane as solvent (Fu G. C. et al., J. Org. Chem., 1999, 64, 10–11; Hartwig. et al., J. Am. Chem. Soc., 2001, 123, 2677–2678). Alternately, compound 15 can be react with 3,3,3-Triethoxy-propyne 22 to produce compound 23. Preferred coupling conditions are dichlorobis(triphenylphosphine)palladium (II) as calatyst, copper (I) idodide as co-catalyst, and triethylamine as base. Compound 23 can be transformed to compound 19 via reduction or conjugate addition to the triple bond. Preferred reduction conditions are chlorotris(triphenylphosphine)rhodium (I) as catalyst under hydrogen atmosphere. In the case of the conjugate addition, preferred conditions are acetylacetonatebis(1,5-cylooctadiene)rhodium (I) as catalyst, in the presence of a suitable alkyl or aryl boronic acid or ester and 2,2'-Bis (diphenylphosphino)-1,1'-binaphthyl (Hayashy T. et al., J. Am. Chem. Soc., 2001, 123, 9918–9919). Compound 19 can be transformed to final compound following Scheme Ic.

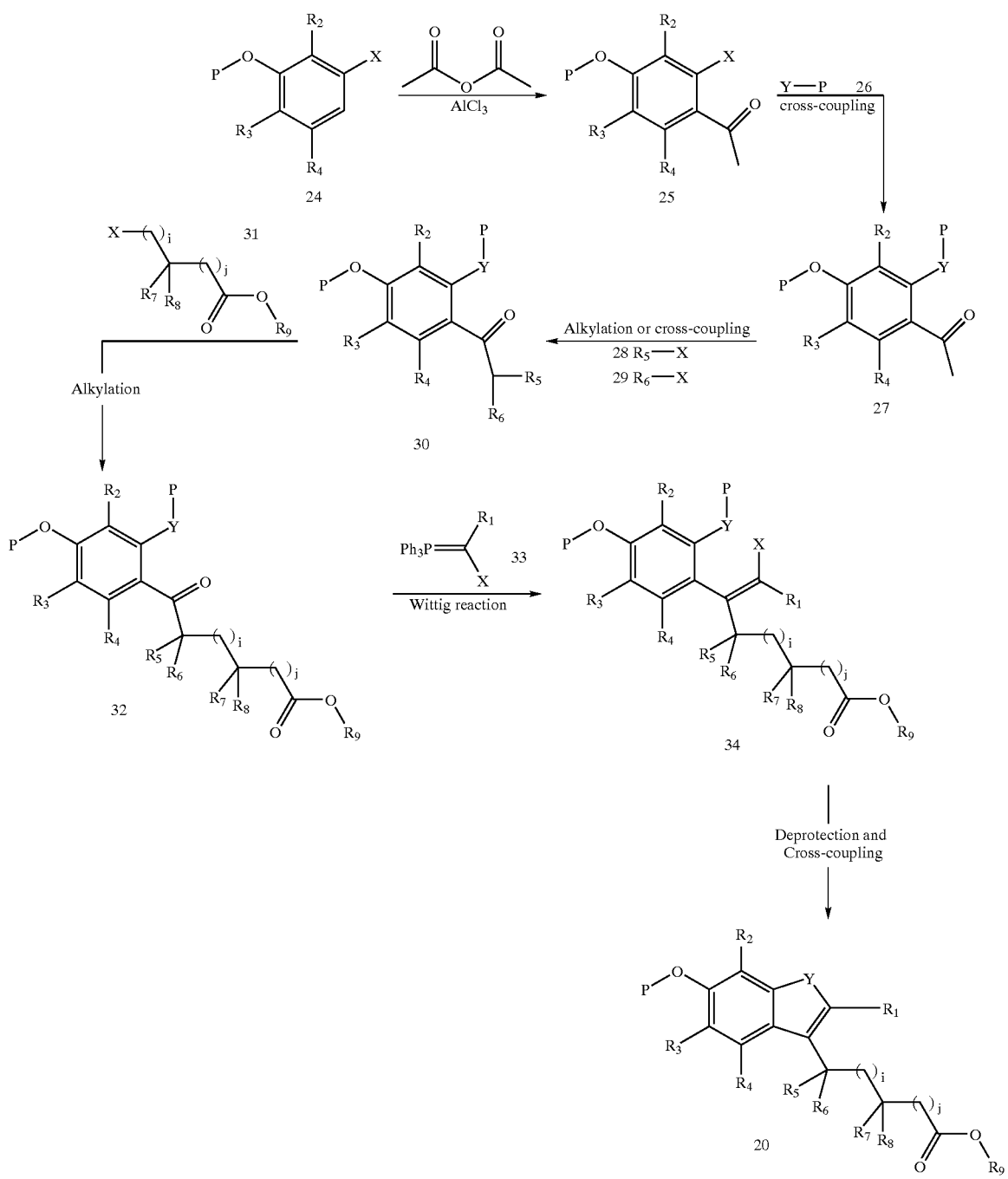

Scheme Ie

In Scheme Ie, compound 24 can be acylated by a Friedel-Crafts reaction. Preferred conditions are the use of an anhydride in the presence of a Lewis acid such as aluminum trichloride to obtain compound 25. Then, cross coupling reaction with the proper thiol or alcohol 26 can be accomplished using an adequate palladium catalyst, a suitable ligand and a base to obtain compound 27. In the case of the thiol, preferred coupling conditions are tris(dibenzylideneacetone)dipalladium (0) as catalyst, 1,1'-Bis(diphenylphosphino)ferrocene as ligand, triethylamine as base and N-N-dimethylformamide as solvent (Ortar, G. et al, Tetrahedron Letters, 1995, 36(23), 4133–4136). In the case of the alcohol, preferred coupling conditions are Palladium (II) acetate as calatyst, [1,1']Binaphthalenyl-2-yl-di-tert-butyl-phosphane as ligand, and cesium carbonate as base ( Stephen Buchwald, personal communication). Compound 27 is reacted with an alkyl halides or an aryl halides, 28 and 29, in the presence of a base to yield compound 30. In the case of the aryl halides the reactions proceed via a cross coupling reaciction. Preferred coupling conditions are palladium (II) acetate as calatyst, Biphenyl-2-yl-di-tert-butyl-phosphane as ligand, and sodium tert-butoxide as base (Buchwald. et al., J. Am. Chem. Soc., 2000, 122, 1360–1370). Compound 30 is alkylated with the alkyl halide 31 to yield compound 32 under standard conditions. Wittig reaction of compound 32 with phosphane 33 produces compound 34. Deprotection and cross coupling reaction of compound 34 yield compound 20.

Scheme IIa, IIb, IIc, IId and IIe outline the synthetic steps to produce compound 3 of the present invention where W is one of:

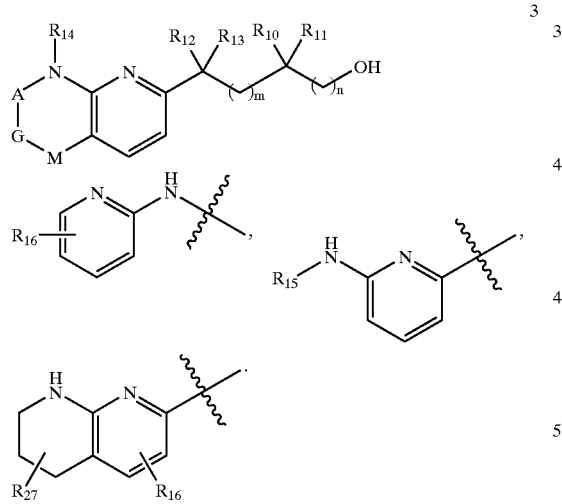

where A, G and M are as defined above, and where $R^{10}$ through $R_{16}$ and $R_{27}$ are as defined above.

Scheme IIa

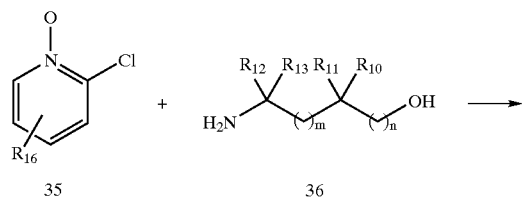

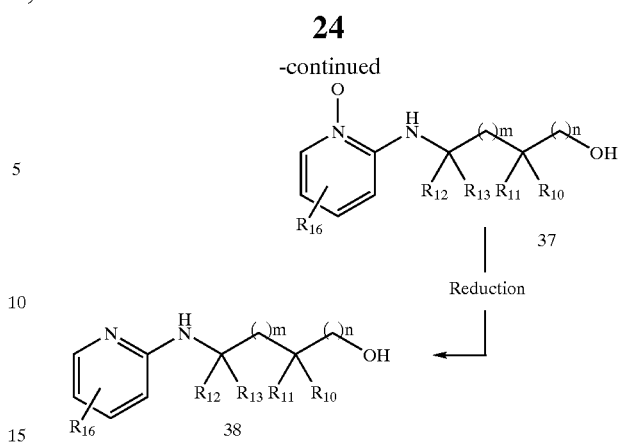

In Scheme IIa, 2-chloropyridine N-oxide derivative 35 is refluxed with aminoalkyl alcohol 36 in the presence of a base, such as sodium bicarbonate, and a suitable solvent, such as tert-amyl alcohol, to give compound 37. Compound 37 is then converted to pyridinyl amninoalkyl alcohol 38 using standard reduction conditions. Preferred conditions include treating compound 37 with cyclohexene in the presence of a catalyst, such as palladium on carbon, and a solvent, such as ethanol.

Scheme IIb

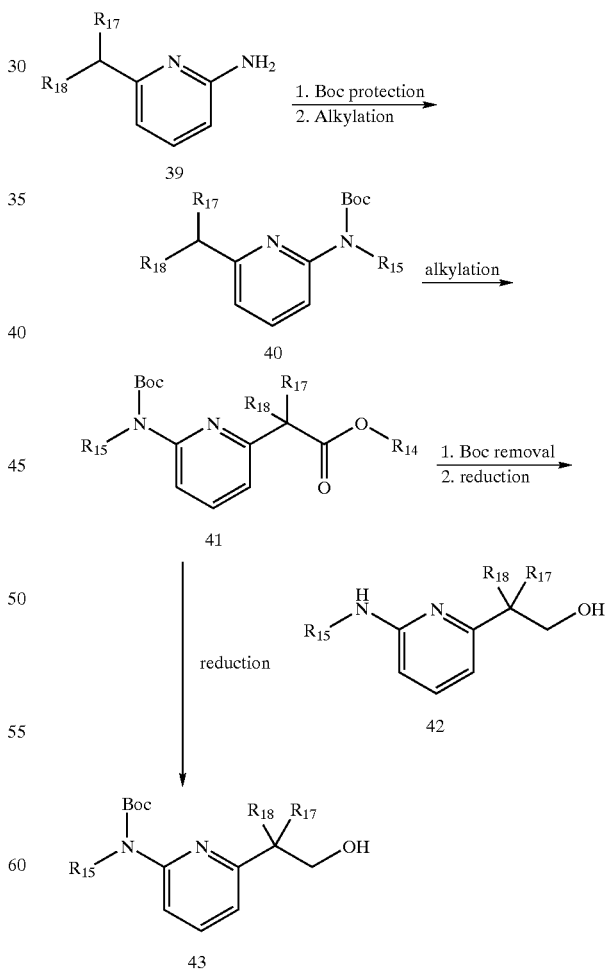

In Scheme IIb, a 2-amino-5-methylpyridine analogue 39 is first protected with a tert-butyloxycarbonyl (Boc) group using conditions well known in art (Greene, T. W. and Wuts, P. G. M., *Protective Groups in Organic Synthesis*, 2nd edition, John Wiley and Sons, Inc., New York (1991)), followed by treatment with an alkyl halide, such as iodomethane, in the presence of a base, such as sodium hydride, and a solvent, such as tetrahydrofuran (THF) or dimethylformamide (DMF), to give compound 40. Converting compound 40 to 41 is accomplished by reacting compound 40 with a base, such as lithium diisopropylamide (LDA), and diethyl carbonate in a solvent, such as tetrahydrofuran (THF). The Boc protecting group of compound 41 is removed by standard procedures well known in the art (Greene, T. W. and Wuts, P. G. M., supra), such as trifluoroacetic acid in methylene chloride. The ester is then reduced by standard conditions, such as lithium aluminum hydride (LAH) in tetrahydrofuran (THF), to give compound 42. Alternatively, compound 41 can be treated with a reducing agent, such as lithium borohydride in a solvent such as tetrahydrofuran to give compound 43.

Scheme IIc

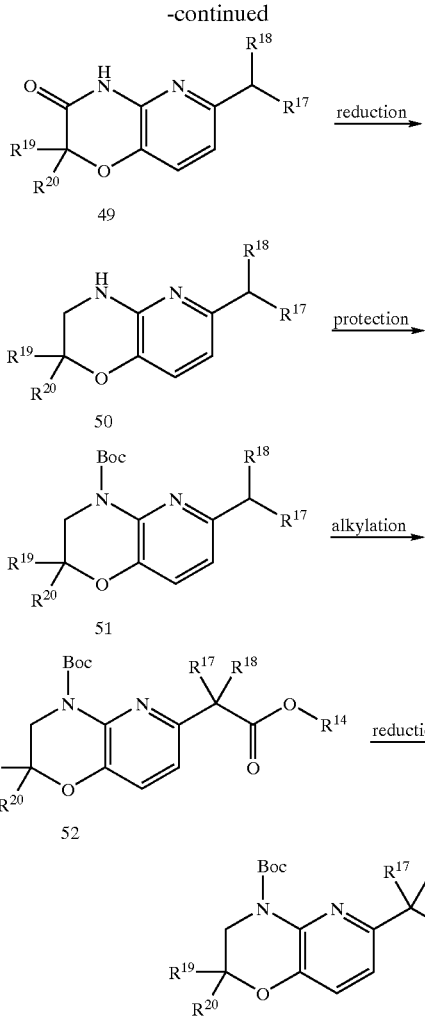

In Scheme IIc, Compound 44 (Miller, H.; Manley, P. J., PCT Int. Appl. No. WO 00/33838) is treated with a reducing agent such as lithium borohydride, in a solvent such as tetrahydrofuran, to give compound 45.

Scheme IId

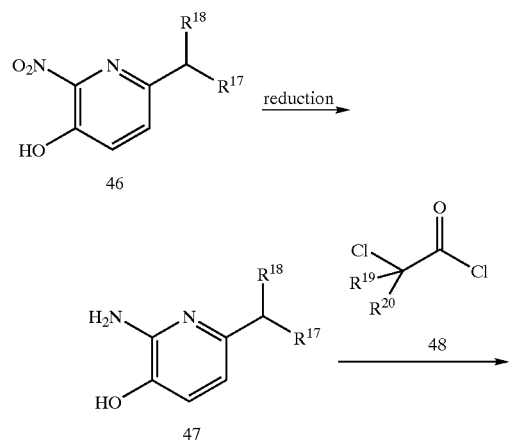

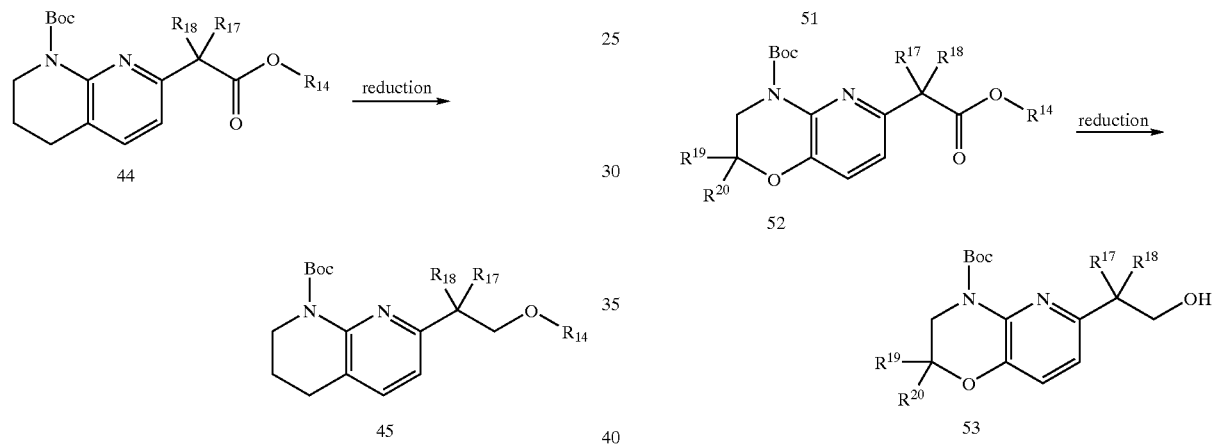

In Scheme IId, 3-hydroxy-6-methyl-2-nitropyridine derivative 46 is reduced under suitable conditions, such as hydrogention in the presence of palladium catalyst, with a solvent, such as ethanol, to give compound 47. Reaction of compound 47 (L. Savelon, et. al., Biorganic and Medicial Chemistry, 6, 133, (1998)) with 2-haloacid chloride 48, such as chloroacetyl chloride, in the presence of base, such as sodium bicarbonate, is suitable solvents, such as water and 2-butanone, gives compound 79. Reduction of compound 49 with suitable reagent, such as lithium aluminum hydride, in a suitable solvent, such as THF, gives compound 50. Compound 50 is protected using suitable conditions, to introduce a protecting group, such as Boc, to give compound 51 (Greene, T. W. and Wuts, P. G. M., *Protective Groups in Organic Synthesis*, 2nd edition, John Wiley and Sons, Inc., New York (1991)). Compound 51 is alkylated under suitable conditions, such as deprotonation with base, such as LDA, followed by reaction with alkylating reagent, such as dialkylcarbonate, to produce compound 52. Reduction of compound 53 is achieved with suitable reducing reagent, such as lithium borohydride in a solvent such as tetrahydrofuran, to give compound 53.

SCHEME III

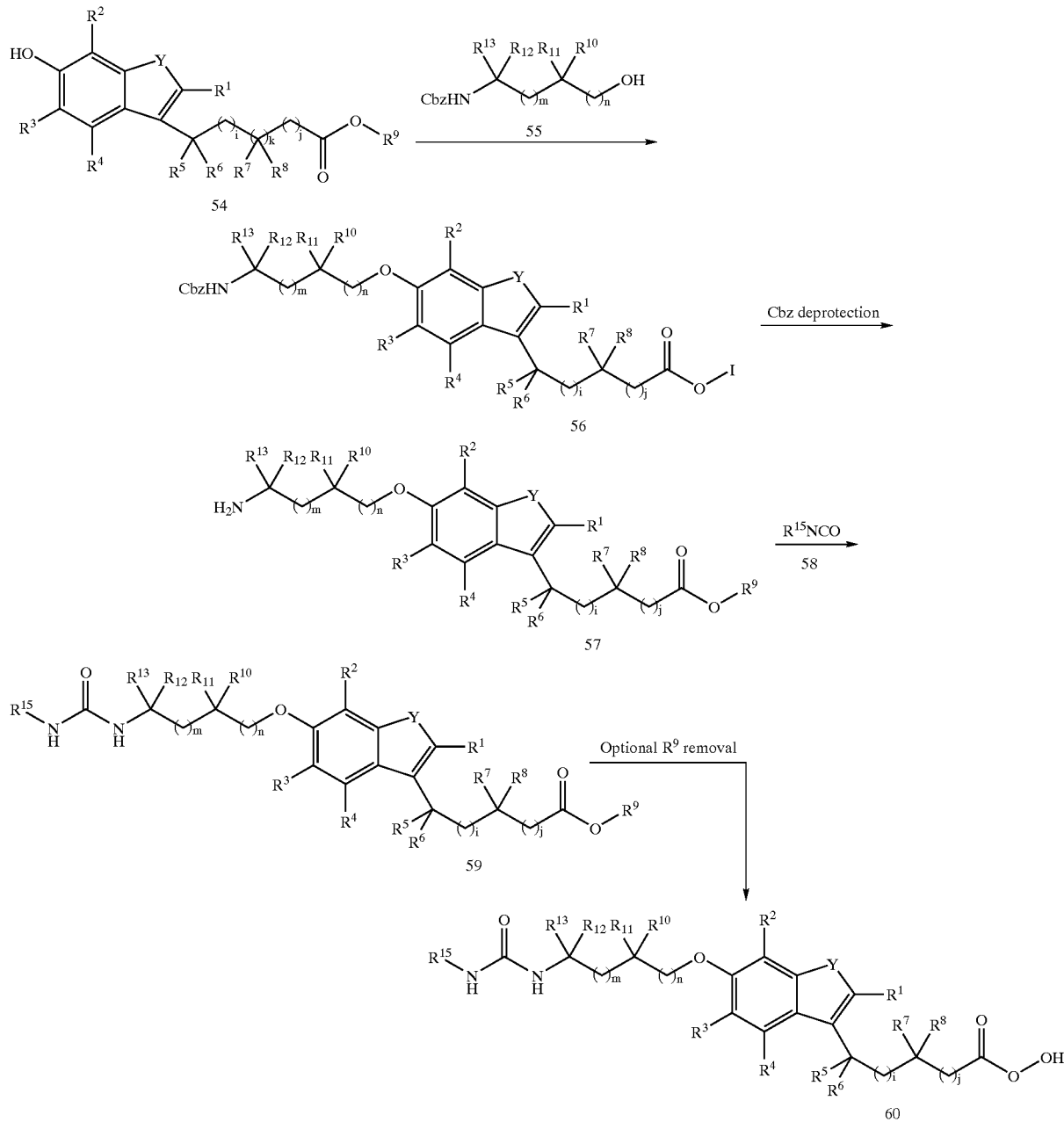

Phenol 54 is coupled to benzyloxycarbonyl (Cbz) protected amino alcohol 55 using a Mitsunobu coupling procedure (Mitsunobu, O., *Synthesis,* 1 (1981)) to give compound 56. Preferred coupling conditions include using a trialkylphosphine or triarylphosphine, such as triphenylphosphine or tri-n-butylphosphine, in a suitable solvent, such as tetrahydrofuran or methylene chloride, and an azodicarbonyl reagent, such as diethyl azodicarboxylate, diisopropyl azodicarboxylate or 1,1'-(azodicarbonyl) dipiperidine.

Deprotection of the Cbz protecting group is accomplished through catalytic hydrogenation using palladium on carbon as a catalyst in solvents such as ethanol or tetrahydrofuran. The amine 57 is treated with isocyanate 58 in a solvent such as acetonitrile to give compound 59. The urea ester 59 may be optionally converted to acid 60 by a standard procedure such as sodium hydroxide in a solvent, such as methanol and water.

Compounds of the present invention can be tested for the ability to inhibit or antagonize $\alpha_v\beta_3$ or $\alpha_v\beta_5$ cell surface receptors by assays known to those of ordinary skill in the art. Such assays are described in Example 4 herein.

The present invention also provides a method of treating $\alpha_v\beta_3$ integrin- or $\alpha_v\beta_5$ integrin-mediated conditions by selectively inhibiting or antagonizing $\alpha_v\beta_3$ and $\alpha_v\beta_5$ cell surface receptors, which method comprises administering a therapeutically effective amount of a compound selected from the class of compounds depicted by Formula I, wherein one or more compounds of Formula I is administered in association with one or more non-toxic, pharmaceutically acceptable carriers and/or diluents and/or adjuvants and if desired other active ingredients.

More specifically, the present invention provides a method for inhibition of the $\alpha_v\beta_3$ cell surface receptor. Most preferably, the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, age-related macular degeneration, retinopathy of prematurity and other neo-vascular eye diseases, inhibiting arthritis, psoriasis and periodontal disease, and inhibiting smooth muscle cell migration including neointimal hyperplasia and restenosis.

The present invention also provides a method for inhibition of the $\alpha_v\beta_5$ cell surface receptor. Most preferably, the present invention provides a method for inhibiting angiogenesis associated with pathological conditions such as inflammatory disorders such as immune and non-immune inflammation, chronic articular rheumatism and psoriasis, disorders associated with inappropriate or inopportune invasion of vessels such as restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and similar cancers which require neovascularization to support tumor growth. The present invention also provides a method for treating eye diseases characterized by angiogenesis, such as diabetic retinopathy, age-related macular degeneration, presumed ocular histoplasmosis, retinopathy of prematurity, and neovascular glaucoma.

The compounds of the present invention are useful in treating cancer, including tumor growth, metastasis and angiogenesis. For example, compounds of the present invention can be employed to treat breast cancer and prostate cancer.

The compounds of the present invention are also useful in the treatment of sickle cell anemia. $\alpha_v\beta_3$-integrin has recently been implicated in the mechanism of adhesion of sickled red blood cells (RBCs) to vascular structures within the circulatory system of those suffering from sickle cell anemia. Adhesion of RBCs is responsible for the reoccurring episodes of painful vasocclusive crisis and multiple organ damage. Kaul et al., Blood 95(2):368–373 (2000). Monoclonal antibodies which bind to $\alpha_v\beta_3$ have been shown to inhibit the adhesion of sickled RBCs in the ex vivo mesocecum vasculature of the rat. Id. By blocking $\alpha_v\beta_3$-integrin which assist in adhesion of sickled cells to vascular components, a reduction in the harmful affects of sickle cell anemia is realized.

The compounds of the present invention are also useful in the treatment of central nervous system (CNS) related disorders. Treatment of such CNS related disorders includes, but is not limited to: treating or preventing neuronal loss associated with stroke, ischemia, CNS trauma, hypoglycemia, and surgery, as well as treating neurodegenerative diseases including Alzheimer's disease, and Parkinson's disease, treating or preventing the adverse consequences of the overstimulation of the excitatory amino acids, as well as treating schizophrenia, anxiety, convulsions, chronic pain, psychosis, including anesthesia, and preventing opiate tolerance.

Studies have shown that there is a correlation between the activity of $\alpha_4$ integrin and the establishment of inflammatory lesions in the CNS. Brocke, S. et al., *Proc. Natl. Acad. Sci. USA* 96:6896–6901 (1999). Specifically, antibodies directed against CD44 and $\alpha_4$ integrin could interfere in several ways with the establishment of inflammatory lesions in the CNS and thus prevent experimental autoimmune encephalomyelitis (EAE), an inflammatory disease of the CNS similar to multiple sclerosis. Brocke at 6899.

Relton and co-workers have also shown that inhibition of $\alpha_4$ integrin activity protects the brain against ischemic brain injury, thereby implicating $\alpha_4$ integrin as a factor in acute brain injury. Relton, et al., *Stroke* 32(1):199–205 (2001).

The compounds of the present invention may be administered in an effective amount within the dosage range of about 0.01 mg/kg to about 300 mg/kg, preferably between 1.0 mg/kg to 100 mg/kg body weight. Compounds of the present invention may be administered in a single daily dose, or the total daily dosage may be administered in divided doses of two, three or four times daily.

The pharmaceutical compositions of the present invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the pharmaceutical preparations of the compounds can contain suitable pharmaceutically acceptable carriers comprising excipients and auxiliaries that facilitate processing of the active compounds into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragee cores are provided with suitable coatings, that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Suitable formulations for parenteral administration include aqueous solutions of the active compounds in water-soluble form, for example water-soluble salts and alkaline solutions. Alkaline salts can include ammonium salts prepared, for example, with Tris, choline hydroxide, bis-Tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

The compounds of the present invention may be administered to the eye in animals and humans as a drop, or within ointments, gels, liposomes, or biocompatible polymer discs, pellets or carried within contact lenses. The intraocular composition may also contain a physiologically compatible ophthalmic vehicle as those skilled in the art can select using conventional criteria. The vehicles may be selected from the known ophthalmic vehicles which include but are not limited to water, polyethers such s polyethylene glycol 400, polyvinyls such as polyvinyl alcohol, povidone, cellulose derivatives such as carboxymethylcellulose, methylcellulose and hydroxypropyl methylcellulose, petroleumn derivatives such as mineral oil and white petrolatum, animal fats such as lanolin, vegetable fats such as peanut oil, polymers of acrylic acid such as carboxylpolymethylene gel, polysaccharides such as dextrans and glycosaminoglycans such as sodium chloride and potassium, chloride, zinc chloride and buffer such as sodium bicarbonate or sodium lactate. High molecular weight molecules can also be used. Physiologically compatible preservatives which do not inactivate the compounds of the present invention in the composition include alcohols such as chlorobutanol, benzalknonium chloride and EDTA, or any other appropriate preservative known to those skilled in the art.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLES

Example 1

Synthesis of 3-(6-{2-[6-(methylamino)-2-pyridyl] ethoxy}benzo [b]thiophen-3-yl)propanoic acid a) Synthesis of 3-Iodophenyl acetate.

A solution of 3-iodophenol (3 g, 13.6 mmol), acetyl chloride (2.9 ml, 40.9 mmol) and potassium carbonate (9.42 g, 68.2 mmol) in N,N-dimethylformamide (75 ml) was stirred for 16 h at room temperature. The mixture was partitioned between water and ethyl acetate. The organic layer was washed with 1N NaOH, dried over magnesium sulfate, and evaporated under vacuum. The crude product was chromatographed over silica gel, eluting with 20% ethyl acetate/hexanes to yield 2.3 g (65%) of 3-iodophenyl acetate.

NMR $^1$H Cl$_3$CD δ: 7.57 (1H, m), 7.46 (1H, m), 7.08 92H, m) 2.29 (3H, s).

b) Synthesis of 3-[1,1-bis(Methylethyl)-2-methyl-1-silapropylthio]phenyl acetate.

Triisopropylsilanethiol (2.91 ml, 13.5 mmol) was added dropwise to a suspension of sodium hydride (325 mg, 13.5 mmol) in THF (10 ml). After the evolution of hydrogen ceased, a solution of 3-iodophenyl acetate (2.37 g, 9.0 mmol) and tetrakis(triphenylphosphine)palladium (0) (1.04 g, 0.9 mmol) in toluene (90 ml) was added. After refluxing for 16 h under argon, the reaction was cooled to room temperature and the solvent was evaporated under vacuum. The resulting residue was dissolved in ethyl acetate, washed with 1N NaOH and brine, dried with sodium sulfate, filtered, and evaporated under vacuum. The crude product was chomatrographed over silica gel to yield 1.53 g (52%) of 3-[1,1-bis (Methylethyl)-2-methyl-1-silapropylthio]phenyl acetate. NMR $^1$H Cl$_3$CD δ: 7.34 (m, 2H), 7.23 (t, 1H, J=2.4 Hz), 6.94 (dd, 1H, J=1.2, 8.4 Hz), 2.28 (s, 3H), 1.25 (m, 3H), 1.08 (d, 18 H, J=7.2 Hz).

c) Synthesis of Ethyl 5-bromo-4-oxopentanoate.

(Trimethylsilyl)diazomethane (34 ml, 67 mmol, 2.0M solution in hexanes) was added dropwise to a solution of ethyl succinyl chloride (5 g, 30.3 mmol) in acetonitrile (60 ml) over a period of 30 minutes. After stirring for 2 h, hydrogen bromide (14 ml, 30% solution in acetic acid) was slowly added over 15 minutes. After the reaction stirred for an additional 1 h, the solvent was evaporated under vacuum. The residue was dissolved in ethyl acetate and washed with 1N NaOH and brine. The organic layer was dried with sodium sulfate, filtered, and evaporated under vacuum to yield 4.3 g (64%) of Ethyl 5-bromo-4-oxopentanoate. NMR $^1$H Cl$_3$CD δ: 4.13 (c, 2H, J=7.2 Hz), 3.96 (s, 2H), 2.95 (t, 2H, J=6.4 Hz), 2.65 (t, 2H, J=6.4 Hz), 1.24 (t, 1H, J=7.2 Hz).

d) Synthesis of Ethyl 5-(3-acetyloxyphenylthio)-4-oxopentanoate.

Tetrabutylammonium fluoride (7 ml, 7.0 mmol, 1M in THF) was added to a solution of 3-[1,1-bis(Methylethyl)-2-methyl-1-silapropylthio]phenyl acetate (1.53 g, 4.7 mmol) in THF (10 ml) under argon at room temperature. The reaction was stirred for 15 minutes followed by addition of a solution of ethyl 5-bromo-4-oxopentanoate (1.15 g, 5.17 mmol) in THF (5 ml). After stirring for 3 hours, the solvent was removed under vacuum and the crude product was chromatographed over silica gel to yield 920 mg (73%) of ethyl 5-(3-acetyloxyphenylthio)-4-oxopentanoate. NMR $^1$H Cl$_3$CD δ: 7.29 (t, 1H, J=8.0 Hz), 7.18 (dd, 1H, J=0.8, 7.6 Hz), 7.07 (t, 1H, J=1.6 Hz), 6.94 (dd, 1H, J=1.2, 8.0 Hz), 4.12 (c, 2H, J=7.2 Hz), 3.75 (s, 2H), 2.89 (t, 2H, J=6.8 Hz), 2.60 (t, 2H, J=6.8 Hz), 2.29 (s, 3H), 1.24 (t, 1H, J=7.2 Hz).

e) Synthesis of Ethyl 3-(6-hydroxybenzo[b]thiophen-3-yl) propanoate.

Concentrated sulfuric acid (20 ml) was cooled in an ice-water bath to 0° C. and added to a flask containing ethyl 5-(3-acetyloxyphenylthio)-4-oxopentanoate (920 mg, 3.4 mmol) at 0° C. The reaction was stirred at 0° C. for 15 minutes, and then poured over ice. The mixture was extracted with ethyl acetate, dried, filtered, and evaporated under vacuum to yield 700 mg (82%) of Ethyl 3-(6-hydroxybenzo[b]thiophen-3-yl)propanoate. NMR $^1$H DMSO-d$_6$ δ: 9.59 (s, 1H), 7.59 (d, 1H, J=8.4 Hz), 7.25 (d, 1H, J=2.4 Hz), 7.08 (s, 1H), 6.89 (dd, 1H, J=2.4, 8.4 Hz), 4.06 (c, 2H, J=7.2 Hz), 2.99 (t, 2H, J=6.8 Hz), 2.70 (t, 2H, J=6.8 Hz), 1.16 (t, 1H, J=7.2 Hz).

f) Synthesis of (tert-Butoxy)-N-(6-methyl(2-pyridyl))carboxamide.

2-Amino-6-picoline (10 g, 92.2 mmol) and di-tert-butyl dicarbonate (22 g, 100.8 mmol) were heated at 50° C. under argon for 16 h. The mixture was cooled to room temperature and poured into ice-water. The reaction was extracted with ethyl acetate, dried with sodium sulfate, filtered, and evaporated under vacuum. The resulting oil was flushed through a plug of silica gel, eluting with 20% ethyl acetate/hexanes to yield 20.2 g (100%) of (tert-Butoxy)-N-(6-methyl (2-pyridyl))carboxamide. NMR $^1$H Cl$_3$CD δ: 7.70 (d, 1H, J=7.6 Hz), 7.54 (t, 1H, J=7.6 Hz), 6.80 (d, 1H, J=7.6 Hz), 2.42 (s, 3H), 1.53 (s, 9H).

g) Synthesis of (tert-Butoxy)-N-methyl-N-(6-methyl(2-pyridyl))carboxamide.

(tert-Butoxy)-N-(6-methyl(2-pyridyl))carboxamide (20.2 g, 102 mmol) dissolved in N,N-dimethylformamide (75 ml) was slowly added to a suspension of sodium hydride (3.67 g, 153 mmol) in DMF (150 ml) at 0° C. The reaction mixture was warmed to room temperature and stirred for 1 h. Methyl iodide (9.5 ml, 153 mmol) was added dropwise at 0° C. After stirring at room temperature for 16 h, the reaction mixture was poured over ice-water and extracted with ethyl acetate. The organic layer was washed with brine, dried with sodium sulfate, filtered, and evaporated under vacuum. The crude product was chromatographed over silica gel to yield 15.3 g (66%) of (tert-Butoxy)-N-methyl-N-(6-methyl(2-pyridyl))carboxamide. NMR $^1$H Cl$_3$CD δ: 7.50 (t, 1H, J=7.6 Hz), 7.37 (d, 1H, J=7.6 Hz), 6.85 (d, 1H, J=7.6 Hz), 3.38 (s, 3H), 2.48 (s, 3H), 1.50 (s, 9H).

h) Synthesis of Ethyl 2-{6-[(tert-butoxy)-N-methylcarbonylamino]-2-pyridyl}acetate.

To a solution of diisopropylamine (6.16 ml, 44 mmol) and TEF (50 ml), at −78° C. under argon, was added butyl-lithium (27 ml, 44 mmol, 1.6 M in hexane) dropwise. The mixture was warmed to room temperature and stirred for 10 minutes. The reaction was cooled to −78° C. and a solution of (tert-Butoxy)-N-methyl-N-(6-methyl(2-pyridyl)) carboxamide (5.0 g, 22 mmol) in THF (100 ml) was added dropwise. The reaction mixture was stirred for 15 minutes at −78° C., followed by addition of diethylcarbonate (4.25 ml, 35 mmol). The mixture was warmed to room temperature and stirred for 2 h. The reaction was quenched with saturated aqueous ammonium chloride and extracted with ethyl acetate. The organic layer was dried with sodium sulfate, filtered, and evaporated under vacuum. The resulting yellow oil was chromatographed over silica gel to yield 2.45 g (38%) of Ethyl 2-{6-[(tert-butoxy)-N-methylcarbonylamino]-2-pyridyl}acetate. NMR $^1$H Cl$_3$CD δ: 7.57 (m, 2H), 6.97 (m, 1H), 4.18 (c, 2H, J=7.2 Hz) 3.76 (s, 2H), 3.42 (s, 3H), 1.51 (s, 9H), 1.27 (t, 3H, J=7.2 Hz).

i) Synthesis of Ethyl 2-[6-(methylamino)-2-pyridyl]acetate.

To a solution of ethyl 2-{6-[(tert-butoxy)-N-methylcarbonylamino]-2-pyridyl}acetate (3.56 g, 12.1 mmol) in dichloromethane (15 ml) was added trifluoroacetic acid (8 ml). The reaction was stirred for 16 h. The solvent was removed under vacuum and the crude product was chromatographed over silica gel to yield 2.2 g (100%) of Ethyl 2-[6-(methylamino)-2-pyridyl]acetate.

NMR $^1$H Cl$_3$CD δ: 7.41 (t, 1H, J=8.0 Hz), 6.55 (d, 1H, J=8.0 Hz), 6.27 (d, 1H, J=8.0 Hz), 4.15 (c, 2H, J=7.2 Hz) 3.64 (s, 2H), 2.88 (d, 3H, J=5.2 Hz), 1.26 (t, 3H, J=7.2 Hz).

j) Synthesis of 2-[6-(Methylamino)-2-pyridyl]ethan-1-ol.

A solution of ethyl 2-[6-(methylamino)-2-pyridyl]acetate (2.2 g, 12.5 mmol) in THF (30 ml) was added dropwise to a suspension of lithium aluminum hydride (1.24 g, 31.2 mmol) in TEF (25 ml) under argon at 0° C. The reaction was stirred for 30 minutes and quenched carefully with water (4 ml) and 1 N NaOH (4 ml). The mixture was filtered through a pad of Celite and washed several times with ethyl acetate. The filtrate was dried with sodium sulfate, filtered, and evaporated under vacuum. The crude product was chromatographed over silica gel to yield 1.50 g (79%) of 2-[6-(Methylamino)-2-pyridyl]ethan-1-ol.

NMR $^1$H Cl$_3$CD δ: 7.35 (dd, 1H, J=7.6, 8.4 Hz), 6.41 (d, 1H, J=7.6 Hz), 6.26 (d, 1H, J=8.4 Hz), 3.96 (t, 2H, J=5.2 Hz), 2.90 (d, 3H, J=5.2 Hz), 2.83 (t, 2H, J=5.2 Hz).

k) Synthesis of 2-[6-(Methylamino)-2-pyridyl]ethyl methylsulfonate.

A mixture of 2-[6-(Methylamino)-2-pyridyl]ethan-1-ol (300 mg, 1.9 mmol), triethylamine (0.3 ml, 2.2 mmol), methanesulfonyl chloride (0.17 ml, 2.2 mmol), and dichloromethane (15 ml) was stirred at 0° C. for 30 minutes. The reaction mixture was diluted with dichloromethane and washed with water. The organic layer was dried with sodium sulfate, filtered, and evaporated under vacuum to give a yellow oil. The crude product was chromatographed over silica gel to yield 300 mg (69%) of 2-[6-(Methylamino)-2-pyridyl]ethyl methylsulfonate. NMR $^1$H Cl$_3$CD δ: 7.45 (dd, 1H, J=7.2, 8.4 Hz), 6.51 (d, 1H, J=7.2 Hz), 6.33 (d, 1H, J=8.4 Hz), 4.65 (t, 2H, J=6.4 Hz), 3.06 (t, 2H, J=6.4 Hz), 2.92 (m, 6H).

l) Synthesis of {6-[2-(3-Iodophenoxy)ethyl](2-pyridyl)}-methylamine.

To a stirring solution of 3-iodophenol (1.11 g, 5.1 mmol), 2-[6-(Methylamino)-2-pyridyl]ethan-1-ol (700 mg, 4.6 mmol), triphenylphosphine (1.3 g, 5.1 mmol), and THF (20 ml), was added diethyl azodicarboxylate (0.80 ml, 5.1 mmol) at 0° C. After stirring overnight under argon at room temperature, the solvent was evaporated under vacuum. The crude product was chromatographed over silica gel to yield 1.2 g (74%) of {6-[2-(3-Iodophenoxy)ethyl](2-pyridyl)}-methylamine. NMR $^1$H Cl$_3$CD δ: 7.40 (t, 1H, J=8.0 Hz), 7.26 (m, 2H), 6.96 (t, 1H, J=8.0 Hz), 6.87 (m, 1H), 6.52 (d, 1H, J=8.0 Hz), 6.25 (d, 1H, J=4.0 Hz), 4.51 (br s, 1H), 4.29 (t, 2H, J=6.8 Hz), 3.07 (t, 2H, J=6.8 Hz), 2.90 (d, 3H, J=8Hz).

m) Synthesis of [6-(2-{3-[1,1-bis(Methylethyl)-2-methyl-1-silapropylthio]phenoxy}ethyl)(2-pyridyl)]methylamine.

To a suspension of sodium hydride (128 mg, 5.1 mmol) in THF (30 ml) was added triisopropylsilanethiol (1.1 ml, 5.1 mmol) dropwise. After the evolution of hydrogen ceased, a solution of {6-[2-(3-Iodophenoxy)ethyl](2-pyridyl)}methylamine (1.2 g, 3.4 mmol) and tetrakis(triphenylphosphine) palladium(0) (390 mg, 0.3 mmol) in toluene (30 ml) was added. After refluxing for 16 h under argon, the reaction mixture was cooled to room temperature and evaporated under vacuum. The residue was dissolved in ethyl acetate and washed with 1N NaOH and brine. The organic layer was dried with sodium sulfate, filtered, and evaporated. The crude product was chomatrographed over silica gel to yield 1.34 g (95%) of [6-(2-{3-[1,1-bis (Methylethyl)-2-methyl- 1-silapropylthio]phenoxy}ethyl)(2-pyridyl)]methylamine. NMR $^1$H Cl$_3$CD δ: 7.38 (dd, 1H, J=7.2, 8.0 Hz), 7.04 (m, 3H), 6.77 (m, 1H), 6.52 (d, 1H, J=8.0 Hz), 6.25 (d, 1H, J=4.0 Hz), 4.29 (t, 2H, J=6.8 Hz), 3.06 (t, 2H, J=6.8 Hz), 2.90 (d, 3H, J=8Hz), 1.85 (m, 3H), 1.09 (m, 2H).

n) Synthesis of ethyl 5-(3-{2-[6-(Methylamino)(2-pyridyl)]ethoxy}phenylthio)-4-oxopentanoate.

To a solution of [6-(2-{3-[1,1-bis(Methylethyl)-2-methyl-1-silapropylthio]phenoxy}ethyl)(2-pyridyl)]methylamine (1.34 g, 3.2 mmol) and THF (25 ml) under Argon, was added tetrabutylamonium floride (3.5 ml, 3.5 mmol, 1M in THF) at room temperature. After stirring for 15 minutes, a solution of ethyl 5-bromo-4-oxopentanoate (0.79 g, 3.5 mmol) in THF (5 ml) was added. The mixture was stirred for 3 h. The solvent was removed under vacuum and the remaining residue was chromatographed over silica gel to yield 830 mg (64%) of Ethyl 5-(3-{2-[6-(Methylamino)(2-pyridyl)]ethoxy }phenylthio)-4-oxopentanoate. NMR $^1$H Cl$_3$CD δ: 7.38 (dd, 1H, J=7.2, 8.0 Hz), 7.17 (t, 1H, J=8.0 Hz), 6.89 (m, 2H), 6.71 (m, 1H), 6.54 (d, 1H, J=8.0 Hz), 6.25 (d, 1H, J=4.0 Hz), 4.30 (t, 2H, J=6.8 Hz), 4.13 (c, 2H, J=7.2 Hz), 3.72 (s, 2H), 3.07 (t, 2H, J=6.8 Hz), 2.91(m, 5H), 2.59 (t, 2H, J=6.8 Hz), 1.24 (t, 3H, J=7.2 Hz).

o) Synthesis of Ethyl 3-(6-{2-[6-(Methylamino)-2-pyridyl]ethoxy}benzo[b]thiophen-3-yl)propanoate.

Method o-1.

Ethyl 3-(6-hydroxybenzo[b]thiophen-3-yl) propanoate (100 mg, 0.4 mmol) was dissolved in a minimal amount of DMF and added carefully to a suspension of sodium hydride (10 mg, 0.4 mmol) in DMF (5 ml) at 0° C. under argon. After stirring for 15 minutes, a solution of 2-[6-(Methylamino)-2-pyridyl]ethyl methylsulfonate (84 mg, 0.36 mmol) in DMF (1 ml) was added. The reaction was stirred at room temperature for 16 h and then poured over ice-water. The product was extracted with ethyl acetate, and washed with 1N NaOH and brine. The organic layer was dried with sodium sulfate, filtered and evaporated under vacuum. The crude product was chromatographed over silica gel to yield 5.8 mg (4%) of Ethyl 3-(6-{2-[6-(methylamino)-2-pyridyl]ethoxy}benzo[b]thiophen-3-yl)propanoate.

Method o-2.

Ethyl 3-(6-hydroxybenzo[b]thiophen-3-yl)propanoate (100 mg, 0.4 mmol) and 4-methylmorpholine (0.05 ml, 0.44 mmol) were dissolved in THF (5 ml) and stirred for 5 minutes. 2-[6-(Methylamino)-2-pyridyl]ethan-1-ol (91 mg, 0.6 mmol), triphenylphosphine (210 mg, 0.8 mmol) and diisopropyl azodicarboxylate (0.16 ml, 0.8 mmol) were added to the mixture sequentially. After stirring overnight under argon, the reaction mixture was partitioned between ethyl acetate and water. The organic layer was dried with sodium sulfate, filtered and evaporated under vacuum. The crude product was chromatographed over silica gel to yield 30 mg (19%) of Ethyl 3-(6-{2-[6-(methylamino)-2-pyridyl]ethoxy}benzo[b]thiophen-3-yl)propanoate.

Method o-3.

Concentrated sulfuric acid (20 ml) was cooled in an ice-water bath to 0° C. and added to a flask containing 5-(3-{2-[6-(Methylamino)(2-pyridyl)]ethoxy}phenylthio)-4-oxopentanoate (830 mg, 2.1 mmol) at 0° C. The reaction was stirred at 0° C. for 15 minutes, and then poured over ice. The solution was neutralized with solid sodium hydrogencarbonate (pH=7) and extracted with ethyl acetate. The organic layer was dried with sodium sulfate, filtered, and evaporated under vacuum to yield 250 mg (30%) of Ethyl 3-(6-{2-[6-(methylamino)-2-pyridyl]ethoxy}benzo[b]thiophen-3-yl)propanoate. NMR $^1$H Cl$_3$CD δ: 7.60 (d, 1H, J=8.8 Hz), 7.38 (dd, 1H, J=7.2, 8.0 Hz), 7.35 (d, 1H, J=2.0 Hz), 7.01 (dd, 1H, J=2.4, 8.8 Hz), 6.93 (m, 1H), 6.56 (d, 1H, J=7.2 Hz), 6.25 (d, 1H, J=8.0 Hz), 4.40 (t, 2H, J=6.8 Hz), 4.15 (c, 2H, J=7.2 Hz), 3.10 (t, 2H, J=6.4 Hz), 2.90 (m, 5H), 2.74 (t, 2H, J=6.4 Hz), 1.25 (t, 1H, J=7.2 Hz).

p) Synthesis of 3-(6-{2-[6-(methylamino)-2-pyridyl]ethoxy}benzo[b]thiophen-3-yl)propanoic acid.

1N NaOH (10 ml) was added to a solution of 3-(6-{2-[6-(Methylamino)-2-pyridyl]ethoxy}benzo[b]thiophen-3-yl)propanoate and THF (10 ml ). The reaction was stirred at room temperature for 16 h. The mixture was diluted with water and ethyl acetate. The separated aqueous layer was neutralized with 1 N HCl to pH=6.5. The resulting precipitate was filtered, washed with distilled water, and dried to yield 74 mg (55%) of 3-(6-{2-[6-(methylamino)-2-pyridyl]ethoxy}benzo[b]thiophen-3-yl)propanoic acid as a white solid. NMR $^1$H DMSO-d$_6$ δ: 7.67 (d, 1H, J=8.0 Hz), 7.58 (d, 1H, J=2.4 Hz), 7.31 (dd, 1H, J=7.2, 8.0 Hz), 7.18 (s, 1H), 7.00 (dd, 1H, J=2.4, 8.0 Hz), 6.45 (d, 1H, J=7.2 Hz), 6.37 (m, 1H), 6.27 (d, 1H, J=8.0 Hz), 4.36 (t, 2H, J=6.4 Hz), 2.99 (t, 2H, J=6.4 Hz), 2.90 (d, 3H, J=8.0 Hz), 2.64 (t, 2H, J=6.4 Hz). Mass Spectrum (LCMS, ESI) calculate for C$_{19}$H$_{21}$N$_2$O$_3$S 357.1 (M+H) found: 357.3.

Example 2

Synthesis of 3-{6-[2-(5,6,7,8-Tetrahydro-[1,8] naphthyridin-2-yl)-ethoxy]-benzo[b]thiophen-3-yl}-propionic acid a) 7-(2-Hydroxy-ethyl)-3,4-dihydro-2H-[1,8]naphthyridine-1-carboxylic acid tert-butyl ester.

7-Ethoxycarbonylmethyl-3,4-dihydro-2H-[1,8] naphthyridine-1-carboxylic acid tert-butyl ester (synthetic methodology described in WO 00/33838) (6.11 g, 19.0 mmol) was dissolved in tetrahydrofuran (40 ml) at room temperature. The solution was place under argon. Lithium borohydride [2M in tetrahydrofuran](22.8 mmol, 11.43 mL) was carefully added and the reaction was refluxed overnight (16 h). The mixture was poured into a solution of saturated ammonium chloride and extracted with ethyl acetate. The organic layer was dried over Na$_2$SO$_4$, filtered, and evaporated under vacuum to give a crude mixture, which was purified via column chromatography to give 7-(2-hydroxy-ethyl)-3,4-dihydro-2H-[1,8]naphthyridine-1-carboxylic acid tert-butyl ester (49% yield). 1H NMR (Cl$_3$CD), δ: 7.30 (d, 1H, J=7.6 Hz), 7.76 (d, 1H, J=7.6 Hz), 3.98 (m, 2H), 3.78 (m, 2H), 2.92 (m, 2H), 2.71 (m, 2H), 1.92 (m, 2H), 1.54 (s, 9H).

7-{2-[3-(2-Ethoxycarbonyl-ethyl)-benzo[b]thiophen-6-yloxy]-ethyl}-3,4-dihydro-2H-[1,8]naphthyridine-1-carboxylic acid tert-butyl ester.

Ethyl 3-(6-hydroxybenzo[b]thiophen-3-yl)propanoate (207 mg, 82.6 mmol), 7-(2-hydroxy-ethyl)-3,4-dihydro-2H-[1,8]naphthyridine-1-carboxylic acid tert-butyl ester (276 mg, 99.2 mmol) and triphenylphosphine (435 mg, 165 mmol) were dissolved in THF (15 ml) and stirred for 15 minutes under argon atmosphere at 0° C. Then, diisopropyl azodicarboxylate (0.325 ml, 165 mmol) was added to the mixture. After stirring overnight under argon, the reaction mixture was partitioned between ethyl acetate and water. The organic layer was dried with sodium sulfate, filtered and evaporated under vacuum. The crude product was chromatographied over silica gel to yield 338 mg (80%) of 7-{2-[3-(2-Ethoxycarbonyl-ethyl)-benzo[b]thiophen-6- yloxy]-ethyl}-3,4-dihydro-2H-[1,8]naphthyridine-1-carboxylic acid tert-butyl ester. NMR $^1$H Cl$_3$CD δ: 7.59 (d, 1H, J=8.8 Hz), 7.33 (m, 2H), 7.00 (dd, 1H, J=2.3, 8.8 Hz), 6.93 (m, 2H), 4.42 (t, 2H, J=6.7 Hz), 4.14 (m, 2H), 3.76 (m, 2H), 3.22 (m, 2H), 3.12 (m, 2H), 2.73 (m, 4H), 1.92 (m, 2H) 1.51 (s, 9H), 1.26 (m, 3H).

c) 7-{2-[3-(2-Carboxy-ethyl)-benzo[b]thiophen-6-yloxy]-ethyl}-3,4-dihydro-2H-[1,8]naphthyridine-1-carboxylic acid tert-butyl ester.

7-{2-[3-(2-Ethoxycarbonyl-ethyl)-benzo[b]thiophen-6-yloxy]-ethyl}-3,4-dihydro-2H-[1,8]naphthyridine-1-carboxylic acid tert-butyl ester (338 mg, 0.66 mmol) was dissolved THF (5ml). Then a solution of sodium hydroxide (132 mg, 3.30 mmol) in water (1 ml) was added. The reaction was stirred at room temperature for 16 hours. After that period, the solvent was evaporated under vacuum and the crude was extracted with ethyl acetate and hydrochloric acid (1M). The organic layer was collected, dried with anhydrous sodium sulfated, filtrated and evaporated under vacuum to yield 268 mg (84%) of 7-{2-[3-(2-Carboxy-ethyl)-benzo[b]thiophen-6-yloxy]-ethyl}-3,4-dihydro-2H-[1,8]naphthyridine-1-carboxylic acid tert-butyl ester. NMR $^1$H Cl$_3$CD δ: 7.59 (d, 1H, J=8.8 Hz), 7.47 (d, 1H, J=7.7 Hz), 7.35 (d, 1H, J=2.3 Hz), 7.05 (d, 1H, J=7.6 Hz), 7.01 (s, 1H), 6.96 (dd, 1H, J=2.3, 8.8 Hz), 4.35 (t, 2H, J=6.5 Hz), 3.73 (m, 2H), 3.18 (m, 2H), 3.05 (m, 2H), 2.72 (m, 2H), 2.66 (m, 2H), 1.88 (m, 2H), 1.49 (s, 9H).

d) 3-{6-[2-(5,6,7,8-Tetrahydro-[1,8]naphthyridin-2-yl)-ethoxy]-benzo[b]thiophen-3-yl}-propionic acid.

7-{2-[3-(2-Carboxy-ethyl)-benzo[b]thiophen-6-yloxy]-ethyl}-3,4-dihydro-2H-[1,8]naphthyridine-1-carboxylic acid tert-butyl ester (168 mg, 0.35 mmol) was dissolved in THF (10 ml). Hydrogen chloride gas was bubbled through the solution until the starting material disappears by TLC. Then the solvent was evaporated under vacuum and the crude was chromatographied over silica gel using 5% methanol/ methylene chloride as solvent to yield 32 mg (24%) of 3-{6-[2-(5,6,7,8-Tetrahydro-[1,8]naphthyridin-2-yl)-ethoxy]-benzo[b]thiophen-3-yl}-propionic acid. NMR $^1$H Cl$_3$CD δ: 7.55 (d, 1H, J=8.7 Hz), 7.25 (m, 2H), 6.93 (s, 1H), 6.88 (dd, 1H, J=2.1, 8.7 Hz), 6.43 (d, 1H, J=7.2 Hz), 4.24 (t, 2H, J=6.1 Hz), 3.45 (m, 2H), 3.10 (m, 4H), 2.71 (m, 4H), 1.88 (m, 2H). Mass Spectrum (LCMS, ESI) calculate for C$_{21}$H$_{23}$N$_2$O$_3$S 383.14 (M+H) found: 383.3.

Example 3

Synthesis of 3-(6-{2-[6-(Methylamino)-2-pyridyl]ethoxy}benzo[b]furan-3-yl)propanoic acid a) Synthesis of 3-[1,1-bis (Methylethyl)-2-methyl-1-silapropoxy]phenyl acetate.

Lithium bis(trimethylsilyl)amide (73 ml, 73 ml, 1M solution in THF) was added dropwise to a solution of resorcinol monoacetate (10 g, 65.7 mmol) in THF (100 ml) at 78° C. under argon. The solution was stirred for 10 minutes and then triisopropylsilyl chloride (15.5 ml, 73 mmol) was added via syringe. After stirring at room temperature overnight, the mixture was partitioned between water and ethyl acetate. The organic layer was dried, filtered and evaporated under vacuum to yield 13 g of crude 3-[1,1-bis(Methylethyl)-2-methyl-1-silapropoxy]phenyl acetate which was used in the next step without further purification. NMR $^1$H Cl$_3$CD δ: 7.19 (t, 1H, J=8 Hz), 6.75 (m, 1H), 6.68 (m, 1H), 6.63 (t, 1H, J=4 Hz), 2.29 (s, 3H), 1.25 (m, 3H), 1.11 (d, 18H, J=7.0 Hz).

b) Synthesis of 3-[1,1-bis(Methylethyl)-2-methyl-1-silapropoxy]phenol.

An aqueous (50 ml) solution of NaOH (3.25 g, 81 mmol) was added to a solution of 3-[1,1-bis(Methylethyl)-2-methyl-1-silapropoxy]phenyl acetate (5 g, 16.2 mmol) in THF (50 ml). After stirring overnight at room temperature, the reaction mixture was partitioned between ethyl acetate and water. The organic layer was washed with brine, dried, filtered, and evaporated under vacuum. The crude product was chromatographed over silica gel to yield 3.89 g (90%) of 3-[1,1-bis(Methylethyl)-2-methyl-1-silapropoxy]phenol. NMR $^1$H Cl$_3$CD δ: 7.06 (t, 1H, J=8.0 Hz), 6.42 (m, 3H), 1.28 (m, 3H), 1.10 (d, 18H, J=7.0 Hz).

c) Synthesis of [6-(2-{3-[1,1-bis(Methylethyl)-2-methyl-1-silapropoxy]phenoxy}ethyl)(2-pyridyl)]methylamine.

To a stirring solution of 3-[1,1-bis(methylethyl)-2-methyl-1-silapropoxy]phenol (200 mg,0.75 mmol),2-[6-(methylamino)-2-pyridyl]ethan-1-ol (104 mg, 0.68 mmol), triphenylphosphine (199 mg, 0.75 mmol) and THF (25 ml), was added diethyl azodicarboxylate (0.12 ml, 0.75 mmol) at 0° C. The reaction was stirred overnight under argon. The solvent was removed under vaccum and the crude product was chromatographed over silica gel to yield 76 mg (28%) of [6-(2-{3-[1,1-bis(Methylethyl)-2-methyl-1-silapropoxy]phenoxy}ethyl)(2-pyridyl)]methylamine. NMR $^1$H Cl$_3$CD δ: 7.39 (m, 1H), 7.07 (t, 1H, J=8.0 Hz), 6.5 (m, 3H), 6.25 (d, 1H, J=8 Hz), 4.27 (t, 2H, J=6.8 Hz), 3.06 (t, 2H, J=6.8 Hz), 2.90 (d, 3H, J=8 Hz), 1.28 (m, 3H), 1.10 (d, 18H, J=7.0 Hz).

d) Synthesis of Ethyl 5-(3-{2-[6-(methylamino)(2-pyridyl)]ethoxy}phenoxy)-4-oxopentanoate.

To a solution of [6-(2-{3-[1,1-bis(Methylethyl)-2-methyl-1-silapropoxy]phenoxy}ethyl)(2-pyridyl)]methylamine (1.60 g, 4.0 mmol) in THF (30 ml) under argon at room temperature, was added tetrabutylammonium fluoride (4.4 ml, 4.4 mmol, 1M in THF). After stirring for 15 minutes, a solution of ethyl 5-bromo-4-oxopentanoate (0.98 g, 4.4 mmol) in THF (5 ml) was added. The mixture was stirred for an additional 3 hours. The solvent was removed under vacuum and the remaining residue was chromatographed over silica gel to yield 860 mg (56%) of Ethyl 5-(3-{2-[6-(methylamino)(2-pyridyl)]ethoxy}phenoxy)-4-oxopentanoate. NMR $^1$H Cl$_3$CD δ: 7.38 (m, 1H), 7.16 (t, 1H, J=8.2 Hz), 7.08 (t, 1H, J=7.9 Hz), 6.64 (m, 1H), 6.45 (m, 3H), 6.26 (dd, 1H, J=8.2, 2.3 Hz), 4.57 (s, 2H), 4.30 (t, 2H, J=6.8Hz), 4.13 (c, 2H, J=7.2 Hz), 3.07 (m, 2H), 2.91 (m, 5H), 2.63 (t, 2H, J=6.6 Hz), 1.24 (t, 3H, J=7.2 Hz).

e) Synthesis of Ethyl 3-(6-{2-[6-(methylamino)-2-pyridyl]ethoxy}benzo[b]furan-3-yl)propanoate.

Concentrated sulfuric acid (3ml) was cooled in an ice-water bath to 0° C. and added to a flask containing ethyl 5-(3-{2-[6-(methylamino)(2-pyridyl)]ethoxy}phenoxy)-4-oxopentanoate (190 mg, 0.5 mmol) at 0° C. The reaction was stirred 15 minutes and then poured over ice. The solution was neutralized with solid sodium hydrogencarbonate (pH= 7) and the product was extracted with ethyl acetate. The organic layer was dried, filtered and evaporated under vacuum to yield 104 mg (57%) of Ethyl 3-(6-{2-[6-(methylamino)-2-pyridyl]ethoxy}benzo[b]furan-3-yl)propanoate. NMR $^1$H Cl$_3$CD δ: 7.36 (m, 3H), 7.01 (d, 1H, J=2.1 Hz), 6.87 (dd, 1H, J=8.5, 2.1 Hz), 6.54 (d, 1H, J=7.2 Hz), 6.23 (d, 1H, J=8.2 Hz), 4.68 (br s, 1H), 4.15 (c, 2H, J=7.4 Hz), 3.09 (t, 2H, J=6.9 Hz), 2.97 (t, 2H, J=6.9 Hz), 2.87 (d, 3H, J=5.1 Hz), 2.68 (t, 2H, J=6.9 Hz), 1.26 (t, 1H, J=7.4 Hz).

f) Synthesis of 3-(6-{2-[6-(Methylamino)-2-pyridyl]ethoxy}benzo[b]furan-3-yl)propanoic acid.

1N NaOH (4 ml) was added to a solution ethyl 3-(6-{2-[6-(methylamino)-2-pyridyl]ethoxy}benzo[b]furan-3-yl)propanoate in THF (4 ml) and stirred for 16 h. The reaction mixture was partitioned between ethyl acetate and water. The aqueous layer was neutralized with 1N HCl (pH=6.5). The resulting precipitate was filtered, rinsed with distilled water, and dried to yield 70 mg (74%) of 3-(6-{2-[6-(Methylamino)-2-pyridyl]ethoxy}benzo[b]furan-3-yl)propanoic acid as a white solid. NMR $^1$H DMSO-$d_6$ δ: 7.54 (dd, 1H, J=7.3, 8.6 Hz), 7.34 (m, 2H), 6.99 (d, 1H, J=2.0 Hz), 6.77 (dd, 1H, J=2.0, 8.6 Hz), 6.53 (d, 1H, J=7.1 Hz), 6.37 (d, 1H, J=7.1 Hz), 6.27 (d, 1H, J=8.5 Hz), 4.19 (t, 2H, J=6.5 Hz), 3.09 (t, 2H, J=6.5 Hz), 2.94 m, 2H), 2.87 (s, 3H), 2.69 (t, 2H, J=6.5 Hz). Mass Spectrum (LCMS, ESI) calculate for $C_{19}H_{21}N_2O_4$ 341.1 (M+H) found: 341.4.

Example 4

In Vitro Inhibition of Purified Enzymes
Fibrinogen-IIb-IIIa Assay

The assay is based on the method of Dennis (Dennis, M. S., et al., *Proteins* 15: 312–321 (1993)). Costar 9018 flat-bottom 96-well ELISA plates were coated overnight at 4° C. with 100 μL/well of 10 μg/mL human fibrinogen (Calbiochem 341578) in 20 mM Tris-HCl pH 7.5, 150 mM NaCl, 2 mM $CaCl_2$, 0.02% $NaN_3$ (TAC buffer), and blocked for 1 hr at 37° C. with 150 μL/well of TAC buffer containing 0.05% Tween 20 and 1% bovine serum albumin (TACTB buffer). After washing 3 times with 200 μL/well of 10 mM $Na_2$ $HPO_4$ pH 7.5, 150 mM NaCl, 0.01% Tween 20 (PBST buffer), controls or test compound (0.027–20.0 μM) were mixed with 40 μg/mL human GPIIbIIIa (Enzyme Research Laboratories) in TACTB buffer, and 100 μL/well of these solutions were incubated for 1 hr at 37° C. The plate was then washed 5 times with PBST buffer, and 100 μL/well of a monoclonal anti-GPIIbIIIa antibody in TACTB buffer (1 μg/mL, Enzyme Research Laboratories MabGP2b3a) was incubated at 37° C. for 1 hr. After washing (5 times with PBST buffer), 100 μL /well of goat anti-mouse IgG conjugated to horseradish peroxidase (Kirkegaard & Perry 14–23–06) was incubated at 37° C. for 1 hr (25 ng/mL in PBST buffer), followed by a 6-fold PBST buffer wash. The plate was developed by adding 100 μL/well of 0.67 mg o-phenylenediamine dihydrochloride per mL of 0.012% $H_2O_2$, 22 mM sodium citrate, 50 mM sodium phosphate, pH 5.0 at room temperature. The reaction was stopped with 50 μL/well of 2M $H_2SO_4$, and the absorbence at 492 nm was recorded. Percent (%) inhibition was calculated from the average of three separate determinations relative to buffer controls (no test compound added), and a four parameter fit (Marquardt, D. W., *J. Soc. Indust. Appl. Math.* 11:431–441 (1963)) was used to estimate the half maximal inhibition concentration ($IC_{50}$).

$α_vβ_3$-vitronectin Assay

The assay was based on the method of Niiya (Niiya, K., et al., *Blood* 70:475–483 (1987)). Costar 9018 flat-bottom 96-well ELISA plates were coated overnight at room temperature with 100 μL/well of 0.4 μg/mL human $α_vβ_3$ (Chemicon CC1019) in TS buffer (20 mM Tris-HCl pH 7.5, 150 mM NaCl, 1 mM $CaCl_2$, 1 mM $MgCl_2$, 1 mM $MnCl_2$). All subsequent steps were performed at room temperature. Plates were blocked for 2 hr with 150 μL/well of TS buffer containing 1% BSA (TSB buffer), and washed 3 times with 200 μL/well of PBST buffer. Controls or test compound (0.0001–20.0 μM) were mixed with 1 μg/mL of human vitronectin (Chemicon CC080) that had been biotinylated in-house with sulfo-NHS-LC-LC-biotin (Pierce 21338, 20:1 molar ratio), and 100 μL/well of these solutions (in TSB buffer) were incubated for 2 hr. The plate was then washed 5 times with PBST buffer, and 100 μL/well of 0.25 μg/mL NeutrAvidin-horseradish peroxidase conjugate (Pierce 31001) in TSB buffer was incubated for 1 hr. Following a 5-fold PBST buffer wash, the plate was developed and results were calculated as described for the fibrinogen-IIbIIIa assay. $IC_{50}$ values for inhibition of the $α_vβ_3$-vitronectin interaction by other compounds of the invention are presented in Table I.

TABLE 1

In Vitro Activity of New $α_vβ_3$ Antagonists

| Example # | $IC_{50}$ (nM) |
|---|---|
| 1 | 30 |
| 2 | 8 |
| 3 | 33 |

$α_vβ_5$-vitronectin assay

The assay is similar to the $α_vβ_3$-vitronectin assay. Costar 9018 flat-botom 96-well ELISA plates are coated overnight at room temperature with 100 μL/well of 1 μg/mL human $α_vβ_5$ (Chemicon CC1023) in TS buffer. Plates are blocked for 2 hr at 30° C. with 150 μL/well of TSB buffer, and washed 3 times with 200 μL/well of PBST buffer. Controls or test compound (0.027–20 μM) are mixed with 1 μg/mL of human vitronectin (Chemicon CC080) that is been biotinylated in-house with sulfa-NHS-LC-LC-biotin (Pierce 21338, 20:1 molar ratio), and 100 μL/well of these solutions (in TSB buffer) are incubated at 30° C. for 2 hr. The plate is then washed 5 times with PBST buffer, and 100 μL/well of 0.25 μg/mL. NeurAvidin-horseradish peroxidase conjugate (Pierce 31001) in TSB buffer is incubated at 30° C. for 1 hr. Following a 6-fold PBST buffer wash, the plate is developed and results are calculated as described for the fibrinogen-IIbIIIa assay.

Example 5

Tablet Preparation

Tablets containing 25.0, 50.0, and 100.0 mg, respectively, of the compound of Example 1 ("active compound") are prepared as illustrated below:

| TABLET FOR DOSES CONTAINING FROM 25–100 MG OF THE ACTIVE COMPOUND | | | |
|---|---|---|---|
| | Amount-mg | | |
| Active compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

Example 6

Intravenous Solution Preparation

An intravenous dosage form of the compound of Example 1 ("active compound") is prepared as follows:

| INTRAVENOUS SOLUTION CONTAINING FROM 0.5–10.0 MG OF THE ACTIVE COMPOUND | |
|---|---|
| Active compound | 0.5–10.0 mg |
| Sodium citrate | 5–50 mg |
| Citric acid | 1–15 mg |
| Sodium chloride | 1–8 mg |
| Water for injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having the Formula I:

or a pharmaceutically acceptable salt, hydrate, or solvate thereof, wherein $R^1$ represents hydrogen, alkyl, haloalkyl, aryl or aralkyl;

$R^2$, $R^3$ and $R^4$ independently represent hydrogen, alkyl, haloalkyl, aryl or aralkyl;

Y is sulfur;

$R^5$, $R^6$, $R^7$ and $R^8$ independently represent: hydrogen; hydroxy; alkyl; haloalkyl; alkoxy; haloalkoxy; cycloalkyl; aryl; or heterocycle having 5–14 ring members, optionally substituted with one or more of halogen, hydroxy, cyano, alkyl, haloalkyl, alkoxy, aryl or arylalkyl, arylalkoxy, aryloxy, alkylsulfonyl, alkyl sulfinyl, alkylalkoxyaryl, mono- or di-alkylamino, aminoalkyl, monoalkylaminoalkyl, dialkylaminoalkyl, alkanoyl, carboxyalkyl; further wherein: aryl or the aryl group of any aryl-containing moiety may be optionally substituted by one or more of: halogen, hydroxy, cyano, alkyl, aryl, alkoxy, haloalkyl, arylalkyl, arylalkoxy, aryloxy, alkylsulfonyl, alkylsulfinyl, alkylalkoxyaryl, mono- or di-alkylamino, aminoalkyl, monoalkylaminoalkyl, dialkylaminoalkyl, alkanoyl, carboxyalkyl;

or $R^5$ and $R^7$ are taken together to form —$(CH_2)_s$—, wherein s is 0 or 1 to 4, while $R^6$ and $R^8$ are defined as above; or $R^6$ and $R^8$ are taken together to form —$(CH_2)_t$—, wherein t is 2 to 8, while $R^5$ and $R^7$ are defined as above; or $R^7$ and $R^8$ are taken together to form —$(CH_2)_u$— wherein u is 2 to 8, while $R^5$ and $R^6$ are defined as above;

i is from 0 to 4;

j is from 0 to 4; and k is 0 or 1;

$R^9$ is hydrogen or a functionality which acts as a prodrug, selected from the group consisting of: alkyl, haloalkyl, aryl, aralkyl, dialkylaminoalkyl, 1-morpholinoalkyl, 1-piperidinylalkyl, pyridinylalkyl, alkoxy(alkoxy)alkoxyalkyl, or (alkoxycarbonyl)oxyethyl, $R^{10}$, $R^{11}$, $R^{12}$ and $R^{13}$ independently represent hydrogen, alkyl, haloalkyl, hydroxyalkyl, aminoalkyl, monoalkylaminoalkyl, dialkylaminoalkyl, carboxylalkyl, aryl or aralkyl;

or $R^{10}$ and $R^{11}$ are taken together to form —$(CH_2)_p$—, where p is 2–8, while $R^{12}$ and $R^{13}$ are defined as above; or $R^{12}$ and $R^{13}$ are taken together to form —$(CH_2)_q$—, where q is 2–8, while $R^{10}$ and $R^{11}$ are defined as above; or $R^{10}$ and $R^{12}$ are taken together to form —$(CH_2)_r$—, while r is zero, 1 or 2, while $R^{11}$ and $R^{13}$ are defined as above;

X represents; oxygen, sulfur, $CH_2$ or NH;

n is from 0 to 4;

m is from 0 to 4;

W is:

wherein:

A, G and M are independently oxygen, sulfur, $CH_2$, CH—$R^a$, C($R^a$)($R^b$), NH or N—$R^a$, wherein $R^a$ and $R^b$, are independently selected from alkyl, haloalkyl or aryl;

Y' is NH, sulfur or CH;

43

Z is N or CH;

R$^{15}$ is hydrogen, alkyl, haloalkyl, aryl or aralkyl; and

R$^{14}$ is hydrogen, alkyl, haloalkyl or halogen.

2. The compound of claim 1, wherein R$^1$ represents hydrogen, C$_{1-6}$ alkyl, C$_{1-6}$ haloalkyl, C$_{6-10}$ aryl or C$_{6-10}$ ar(C$_{1-6}$)alkyl.

3. The compound of claim 2, wherein R$^1$ represents hydrogen, methyl, ethyl, propyl, butyl, fluoromethyl, fluoroethyl, fluoropropyl, fluorobutyl, phenyl, benzyl or phenylethyl.

4. The compound of claim 1, wherein R$^2$, R$^3$ and R$^4$ independently represent hydrogen, C$_{1-6}$ alkyl, C$_{1-6}$ haloalkyl, C$_{6-10}$ aryl, or C$_{6-10}$ ar(C$_{1-6}$)alkyl.

5. The compound of claim 1, wherein R$^2$, R$^3$ and R$^4$ are hydrogen, C$_{1-4}$ alkyl or C$_{1-4}$ haloalkyl.

6. The compound of claim 1, wherein R$^{10}$, R$^{11}$, R$^{12}$ and R$^{13}$ independently represent hydrogen, C$_{1-4}$ alkyl or C$_{1-4}$ haloalkyl.

7. The compound of claim 1, wherein X is oxygen or CH$_2$.

8. The compound of claim 1, wherein W is

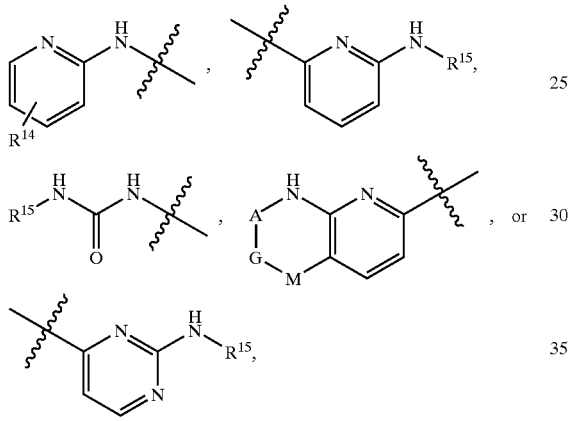

wherein:

A, G and M are independently oxygen, sulfur, CH$_2$, CH—R$^a$, C(R$^a$)(R$^b$), NH or N—R$^a$, wherein R$^a$ and R$^b$, are independently selected from C$_{1-6}$ alkyl, C$_{1-6}$ haloalkyl or C$_{6-10}$ aryl;

R$^{15}$ is hydrogen, C$_{1-6}$ alkyl, C$_{1-6}$ haloalkyl or C$_{6-10}$ ar(C$_{1-6}$)alkyl; and R$^{14}$ is hydrogen, C$_{1-4}$ alkyl or C$_{1-4}$ haloalkyl.

9. The compound of claim 1, wherein R$^5$, R$^6$, R$^7$ and R$^8$ independently represent hydrogen, C$_{1-6}$ alkyl, C$_{1-6}$ haloalkyl, C$_{3-6}$ cycloalkyl, C$_{6-10}$ aryl, C$_{6-10}$ ar(C$_{1-6}$)alkyl, C$_{1-6}$aminoalkyl, mono(C$_{1-4}$alkylamino(C$_{1-6}$)alkyl, di(C$_{1-4}$-alkylamino(C$_{1-6}$)alkyl, carboxy (C$_{1-6}$) alkyl, hydroxy, C$_{1-6}$ alkoxy, mono(C$_{1-4}$)alkylamino or di((C$_{1-4}$)alkylamino.

10. The compound of claim 1, wherein R$^5$ and R$^7$ are taken together to form —(CH$_2$)$_s$— where s is zero or 1 to 4, and R$^6$ and R$^8$ are each hydrogen.

11. The compound of the claim 1, wherein R$^5$ and R$^6$ are taken together to form —(CH$_2$)—$_t$, where t is 2 to 5 and R$^7$ and R$^8$ are each hydrogen.

12. The compound of claim 1, wherein i and j are 0.

13. The compound of claim 12, wherein k is 1.

14. The compound of claim 1, wherein R$^9$ hydrogen.

15. The compound of claim 1, wherein i and j are each zero; k is one; R$^5$, R$^6$ and R$^7$ are each hydrogen; and R$^8$ is hydrogen, C$_{1-6}$ alkyl, C$_{1-6}$ haloalkyl, C$_{6-10}$ aryl or C$_{6-10}$ ar(C$_{1-4}$)alkyl.

16. The compound of claim 1, wherein

44

R$^1$ is hydrogen or —CH$_3$;

R$^2$, R$^3$, R$^4$, R$^{10}$, R$^{11}$, R$^{12}$ and R$^{13}$ are hydrogen; X is oxygen or CH$_2$;

n is 0 or 1;

m is 0 or 1;

R$^5$, R$^6$, R$^7$ and R$^8$ independently represent hydrogen, C$_{1-6}$ alkyl, C$_{1-6}$ haloalkyl or C$_{6-10}$ aralkyl;

or one of the combination R$^5$ and R$^7$, R$^6$ and R$^8$, or R$^7$ and R$^8$ are taken together to form —(CH$_2$)$_s$—, —(CH)t—, or —(CH2)u—, wherein s, t, or u is 1 while the remaining R$^5$–R$^8$ are defined above;

i is 0 or 1;

j is 0 or 1;

k is 0 or 1;

R$^9$ is hydrogen or alkyl;

W is:

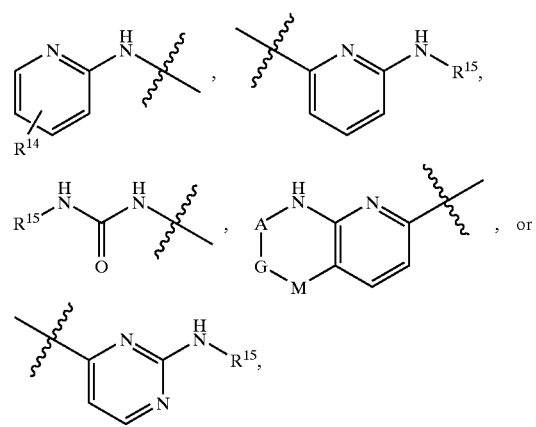

wherein:

A, G and M are independently oxygen, sulfur, CH$_2$, CH—R$^a$, C(R$^a$)(R$^b$), NH or N—R$^a$, wherein R$^a$ and R$^b$, are independently selected from C$_{1-6}$ alkyl, C$_{1-6}$haloalkyl or C$_{6-10}$ aryl;

R$^{15}$ is C$_{6-10}$ ar(C$_{1-6}$)alkyl; and

R$^{14}$ is hydrogen, C$_{1-4}$alkyl or C$_{1-4}$ haloalkyl.

17. The compound of claim 1, which is one of:

3-(6-{2-[6-methylamino)-2-pyridyl]ethoxy}benzo[b]thiophen-3-yl)propanoic acid;

3-quinolin-3-yl-3-{6-[2-(5,6,7,8-tetrahydro-[1,8] naphthyridin-2-yl)-ethoxy]-benzo[b]thiophen-3-yl}-propionic acid;

3-{6-[2-(6-methylamino-pyridin-2-yl)-ethoxy]-benzo[b]thiophen-3-yl}-3-quinolin-3-yl-propionic acid;

3-(2,3-dihydro-benzofuran-6-yl)-3-{6-[2-(5,6,7,8-tetrahydro-[1,8]naphthyridin-2-yl)-ethoxy]-benzo[b]thiophen-3-yl}-propionic acid;

3-(2,3-dihydro-benzofuran-6-yl)-3-{6-[2-(6-methylamino-pyridin-2-yl)-ethoxy]-benzo[b]thiophen-3-yl}-propionic acid;

3-benzo[1,3]dioxol-5-yl-3-{6-[2-(3,4-dihydro-2H-pyrido[3,2-b][1,4]oxazin-6-yl)-ethoxy]-benzo[b]thiophen-3-yl}-propionic acid;

3-benzo[1,3]dioxol-5-yl-3-{6-[2-(5,6,7,8-tetrahydro-[1,8]naphthyridin-2-yl)-ethoxy]-benzo[b]thiophen-3-yl}-propionic acid;

3-benzo[1,3]dioxol-5-yl-3-{6-[2-(6-methylamino-pyridin-2-yl)-ethoxy]-benzo[b]thiophen-3-yl}-propionic acid;

3pyridin-3-yl-3-{6-[2-(5,6,7,8-tetrahydro-[1,8]naphthyridin-2-yl)-ethoxy]-benzo[b]thiophen-3-yl}-propionic acid;

3-(5-aryl-pyridin-3-yl)-3-{6-[2-(5,6,7,8-tetrahydro-[1,8]naphthyridin-2-yl)-ethoxy]-benzo[b]thiophen-3-yl}-propionic acid;

or a pharmaceutically acceptable salt, hydrate, solvate or prodrug thereof.

18. A pharmaceutical composition comprising a compound of claim 1 and a pharmaceutically acceptable carrier or diluent.

19. A process for preparing compound of claim 1, comprising: reacting a compound of Formula II:

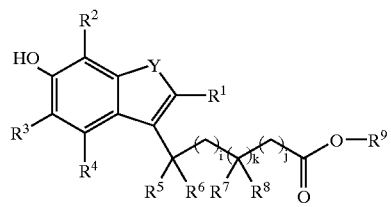

or a salt, hydrate or solvate thereof, wherein $R^1$, $R^2$, $R^3$, $R^4$, $R^5$, $R^{10}$, $R^{11}$, $R^{12}$, $R^{13}$, $R^{14}$, i, j and k are as defined in claim 1, with a compound of Formula IV:

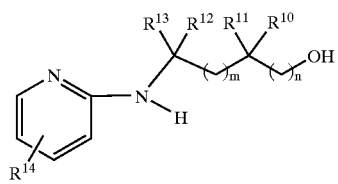

or a salt, hydrate or solvate thereof, wherein $R^{10}$, $R^{11}$, $R^{12}$, $R^{13}$, $R^{14}$, m and n are as defined in claim 1, to form a compound of claim 1.

20. A process for preparing a compound of claim 1, comprising: reacting a compound of Formula V:

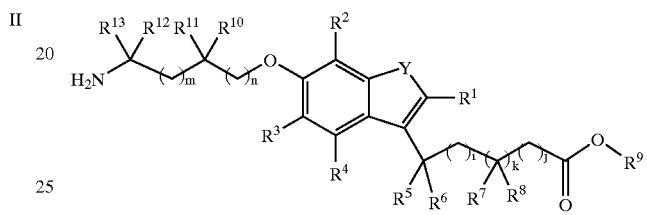

or a salt, hydrate or solvate thereof, wherein
$R^1$, $R^2$, $R^3$, $R^4$, $R^5$, $R^6$, $R^7$, $R^8$, $R^9$, $R^{10}$, $R^{11}$, $R^{12}$, $R^{13}$, i, j, k, m and n are as defined in claim 1,
with $R^{15}$NCO, where $R^{15}$ is as defined in claim 1, to form a compound of claim 1.

* * * * *